(12) United States Patent
Wang

(10) Patent No.: US 9,475,894 B2
(45) Date of Patent: Oct. 25, 2016

(54) DENDRITIC POLYMER, DENDRITIC POLYMER MONOMER, AND HYPERBRANCHED COPOLYMER

(71) Applicants: CHINA PETROLEUM & CHEMICAL CORPORATION, Beijing (CN); SINOPEC ZHONGYUAN OILFIELD SERVICE CORPORATION DRILLING ENGINEERING RESEARCH INSTITUTE, Puyang (CN)

(72) Inventor: Zhonghua Wang, Puyang (CN)

(73) Assignees: CHINA PETROLEUM & CHEMICAL CORPORATION, Beijing (CN); SINOPEC ZHONGYUAN OILFIELD SERVICE CORPORATION DRILLING ENGINEERING RESEARCH INSTITUTE, Puyang (CN)

( * ) Notice: Subject to any disclaimer, the term of this patent is extended or adjusted under 35 U.S.C. 154(b) by 18 days.

(21) Appl. No.: 14/314,756

(22) Filed: Jun. 25, 2014

(65) Prior Publication Data

US 2014/0378638 A1  Dec. 25, 2014

(30) Foreign Application Priority Data

Jun. 25, 2013 (CN) .......................... 2013 1 0256162
Jun. 25, 2013 (CN) .......................... 2013 1 0256842

(51) Int. Cl.
C08F 22/38    (2006.01)
C08F 220/58   (2006.01)
C08F 220/60   (2006.01)
C08F 222/06   (2006.01)

(52) U.S. Cl.
CPC ............. *C08F 22/38* (2013.01); *C08F 220/58* (2013.01); *C08F 220/60* (2013.01); *C08F 222/06* (2013.01)

(58) Field of Classification Search
CPC  C08G 83/002; C08G 83/004; C08G 83/005; C08G 83/006; C08G 73/028
USPC ........................................ 526/287
See application file for complete search history.

(56) References Cited

U.S. PATENT DOCUMENTS

| | | | | |
|---|---|---|---|---|
| 3,984,408 A | * | 10/1976 | Lamberti | C07C 291/04 544/110 |
| 4,587,304 A | * | 5/1986 | Thaler | C08F 8/46 525/284 |
| 4,737,303 A | * | 4/1988 | Thaler | C08F 8/34 508/233 |
| 4,939,283 A | | 7/1990 | Yokota et al. | |
| 5,296,627 A | | 3/1994 | Tang et al. | |
| 5,472,642 A | * | 12/1995 | Gutierrez | C07C 309/18 510/305 |
| 6,649,718 B2 | | 11/2003 | Nishitani et al. | |
| 7,026,418 B2 | | 4/2006 | Schulz et al. | |
| 2006/0182922 A1 | * | 8/2006 | Ishida | C08G 18/0828 428/44 |
| 2007/0265468 A1 | * | 11/2007 | Twyman | C08G 73/028 562/561 |
| 2010/0079866 A1 | * | 4/2010 | Radcliffe | G02B 1/111 359/581 |
| 2011/0182843 A1 | * | 7/2011 | Derks | A61K 8/85 424/70.17 |
| 2015/0136698 A1 | * | 5/2015 | Bothof | C08G 69/48 210/651 |

FOREIGN PATENT DOCUMENTS

CN   101429427 A   5/2009
CN   101982224     3/2011

(Continued)

OTHER PUBLICATIONS

Wang Zhonghua, "The Design Ideas for High-performance Drilling Fluid Additives," Sino-Global Energy, 2013, vol. 18 (1), pp. 36-46 and an English abstract thereof.

(Continued)

*Primary Examiner* — Mike M Dollinger
(74) *Attorney, Agent, or Firm* — Buchanan Ingersoll & Rooney PC

(57) ABSTRACT

A dendritic polymer, a dendritic polymer monomer, and a hyperbranched copolymer are described. The dendritic polymer monomer has a structure denoted by Z'-(Q)n-Y, wherein Z' represents a structure denoted by the following formula (a) and/or formula (b), Q represents a dendritic constitutional repeating unit of the dendritic polymer monomer, n represents the generation number of the dendritic polymer monomer, and is an integer within a range of 2-6, Y represents a group that contains $SO_3^-$ or $COO^-$, $R_{14}$-$R_{16}$ can be identical to or different from each other, and are H or $C_1$-$C_5$ alkyl respectively. The monomer can be used as a copolymerizable monomer for preparing a hyperbranched polymer applicable to oil fields, the obtained hyperbranched polymer can be used as an inhibiting filtrate reducer for drilling fluid, flocculating agent, encapsulating agent, heat-resistant and salinity-resistant polymer flooding agent, and thickening agent for fracturing liquid, etc.

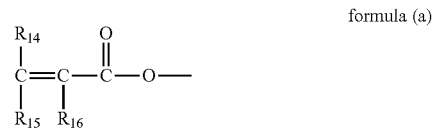

formula (a)

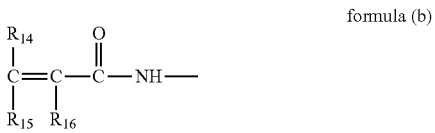

formula (b)

6 Claims, No Drawings

(56) References Cited

FOREIGN PATENT DOCUMENTS

| CN | 102234374 A | 11/2011 |
|---|---|---|
| CN | 102260489 A | 11/2011 |
| CN | 102489215 A | 6/2012 |
| DE | 102011054396 A1 | 4/2013 |
| WO | 2010096388 A2 | 8/2010 |

OTHER PUBLICATIONS

Office Action and Search Report issued May 5, 2016, by the State Intellectual Property of China, in corresponding Chinese Patent Application No. 201310256162.7 and English translations of the Office Action and Search Report (13 pages).

Wang, Z., "The Design Ideas for High-Performance Drilling Fluid Additives," Sino-Global Energy, vol. 18, No. 1, Jan. 31, 2013, pp. 36-46, and an English abstract.

Li, et al., "Synthesis and application of dendrimers in oilfield chemistry," Modem Chemical Industry, vol. 32, No. 6, Jun. 2012, pp. 16-21, and an English abstract.

Hamidi, et al., "Novel Aldehyde-Terminated Dendrimers; Synthesis and Cytotoxicity Assay," BioImpacts, 2012, vol. 2, No. 2, pp. 97-103.

Abstract of Buczkowski et al., "Interaction between PAMAM—NH2 G0 dendrimer and dissociated sodium chloride in aqueous solution", Journal of Molecular Liquids, 2012, vol. 171, pp. 54-59.

\* cited by examiner

DENDRITIC POLYMER, DENDRITIC POLYMER MONOMER, AND HYPERBRANCHED COPOLYMER

CROSS REFERENCE TO RELATED APPLICATIONS

This application claims the priority to Chinese Application No. 201310256842.9 and 201310256162.7, both filed on Jun. 25, 2013, entitled "Hyperbranched Copolymer and Preparation Method and Use thereof" and "Dendritic Polymer, Dendritic Polymer Monomer and Preparation Method and Use thereof" respectively, which are specifically and entirely incorporated by reference.

FIELD OF THE INVENTION

The present invention relates to a dendritic polymer, a dendritic polymer monomer, and a hyperbranched copolymer.

BACKGROUND OF THE INVENTION

In emulsion polymerization field, if emulsion or inverse emulsion is obtained with an appropriate surfactant, the product quality of the application system will be greatly improved; however, the residual surfactant after polymerization reaction will result a series of problems. Up to now, some polymerizable surfactants applicable to emulsion polymerization have been proposed in many patent literatures. For example, U.S. Pat. No. 4,939,283 discloses a polymerizable surfactant obtained from the reaction between a conventional non-ionic surfactant and allyloxyglycidol ether; U.S. Pat. No. 5,296,627 discloses an ethylene terminated allyloxypolymerizable surfactant; U.S. Pat. No. 6,649,718 discloses a polymerizable surfactant obtained from the reaction between long-chain alkylene oxide and allyl alcohol; U.S. Pat. No. 7,026,418 discloses a surfactant prepared from a copolymer of alkylene oxide with polymerizable double bonds and glycidol ether; CN102489215A discloses an amphoteric reacting surfactant; CN101982224A discloses a polymerizable surfactant that contains allyl or methyl allyl and is obtained by etherification between a glycidol ether compound and allyl alcohol or methyl allyl alcohol and follow-up epoxy addition.

In the petroleum drilling course, the encountered formations are more and more complex, and exceptional wells, ultra-deep wells, and complex wells increase with years, bringing higher requirements for the drilling fluid. In the development of unconventional oil and gas, typically shale gas, 60%-70% horizontal wells of shale gas in foreign countries employ oil base drilling fluid systems for well drilling, to meet the requirement for well wall stability, lubrication and sticking prevention. However, water-based drilling fluids are the best choice, because oil-based drilling fluids have high cost and environmental pollution problems. It is found in researches that active shale suffers water loss (or dehydration) in dense $CaCl_2$ solution, therefore, it is necessary to study the application of water-based $CaCl_2$/polymer drilling fluids for horizontal drilling of shale gas for the purpose of cost reduction and environmental protection. Since linear polymers can't fully meet the requirements of well drilling owing to the fact that their tackifying ability is degraded under high-salinity conditions, a key task in the development of water-based $CaCl_2$/polymer drilling fluids is to develop a polymer treating agent applicable to water-based $CaCl_2$/polymer drilling fluids.

SUMMARY OF THE INVENTION

The object of the present invention is to provide a dendritic polymer, a dendritic polymer monomer and a hyperbranched copolymer, which can effectively improve heat resistance, salinity resistance and inhibition properties of oil-displacing agents, and can be used for preparation of a water-based $CaCl_2$/polymer drilling fluid, and a preparation method and use thereof.

The present invention provides a dendritic polymer, having a structure denoted by Z-(Q)n-Y, wherein Z represents a group that can have condensation reaction with acyl halides; Q represents a dendritic constitutional repeating unit of the dendritic polymer; n represents the generation number of the dendritic polymer, and is an integer within a range of 2-6; and Y represents a group containing $SO_3^-$ and $COO^-$.

Moreover, the present invention provides a dendritic polymer monomer having a structure denoted by Z'-(Q)n-Y, wherein Z' represents a structure denoted by the following formula (a) and/or formula (b); Q represents a dendritic constitutional repeating unit of the dendritic polymer monomer; n represents the generation number of the dendritic polymer monomer, and is an integer within a range of 2-6; and Y represents a group containing $SO_3^-$ and $COO^-$,

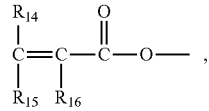

formula (a)

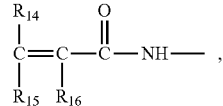

formula (b)

$R_{14}$-$R_{16}$ are identical to or different from each other, and are H or $C_1$-$C_5$ alkyl respectively.

Furthermore, the present invention provides a hyperbranched copolymer containing dendritic structural units A, amphoteric ion structural units B, structural units C, and structural units D, and calculated in moles, the ratio of dendritic structural unit A:amphoteric ion structural unit B:structural unit C:structural unit D=0.03-0.35:0.03-0.5: 0.03-0.3:0.15-0.95, preferably the ratio of dendritic structural unit A:amphoteric ion structural unit B:structural unit C:structural unit D=0.05-0.25:0.05-0.3:0.05-0.15:0.25-0.65, and the apparent viscosity of 1 mass % water solution of the hyperbranched copolymer is 20-60 mPa·s, wherein the dendritic structural unit A has a structure denoted by Z'-(Q)n-Y, wherein Z' represents a structure denoted by the following formula (a1) and/or formula (a2); Q represents a dendritic constitutional repeating unit of the dendritic structure; n represents the generation number of the dendritic structure, and is an integer within a range of 2-6; and Y represents a group containing $SO_3^-$ and $COO^-$,

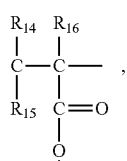
formula (a1)

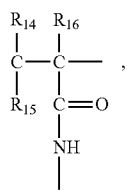
formula (a2)

$R_{14}$-$R_{16}$ are identical to or different from each other, and are H or $C_1$-$C_5$ alkyl respectively;

the amphoteric ion structural unit B has a structure denoted by the following formula (b1) and/or formula (b2),

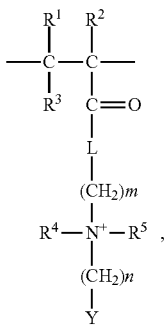
formula (b1)

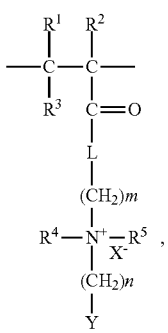
formula (b2)

in formula (b1) and formula (b2), $R^1$, $R^2$, $R^3$, $R^4$ and $R^5$ are H or $C_1$-$C_3$ alkyl respectively, in and n are an integer within a range of 0-5 respectively, and L is O or NH; in formula (b1), Y is $COO^-$ or $SO_3^-$; in formula (b2), $X^-$ is halogen anion, and R is H or hydroxyl-substituted $C_1$-$C_3$ alkyl;

the structural unit C has a structure denoted by the following formula (c);

the structural unit D has a structure denoted by the following formula (d),

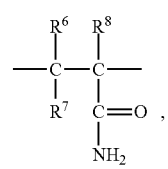
formula (c)

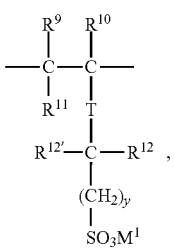
formula (d)

In formula (c), $R^6$, $R^7$ and $R^8$ are H or $C_1$-$C_3$ alkyl respectively; in formula (d), $R^9$, $R^{10}$, $R^{11}$, $R^{12}$ and $R^{12'}$ are H or $C_1$-$C_3$ alkyl respectively, T is a bond or

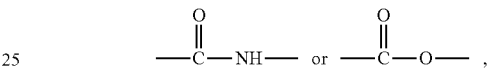

$M^1$ is H or an alkali metal element, and y is an integer within a range of 1-4.

A polymer prepared from coordination of the dendritic polymer and dendritic polymer monomer disclosed in the present invention with other monomers such as acrylamide can effectively improve heat resistance, salinity resistance and inhibition properties, and water-solubility of polymer treating agents for drilling fluids. When the hyperbranched copolymer provided in the present invention is used as a treating agent for a hyperbranched amphoteric ion polymer for drilling fluid, the drilling fluid can meet the demand for safe well drilling operation in an environment with 100° C. or higher well-bottom temperature and/or high salinity (sodium chloride) and high calcium content, the rheological property and filtrate loss of a water-based drilling fluid under high-temperature and high-pressure conditions can be controlled, and the inhibiting ability of the drilling fluid can be improved. For example, it can be seen from the outcomes in the attached Table 1: with a polymer treating agent prepared from the dendritic polymer monomer prepared in Preparation Example 3 of the present invention, when measured after aging for 16 h at 180° C., the API filtrate loss is reduced to 14.5 ml when compared with 89 ml API filtrate loss in the case that the dendritic polymer monomer is not added, which means the reduction rate is as high as 83.8%. In addition, the inhibiting ability $R_1$ is improved to 96.1% and the viscosity retentivity is improved to 34.5%, when compared with the respective 91.5% and 15.2% values in the case that the dendritic polymer monomer is not added. Moreover, since the polymer contains water-soluble groups, it has high water-solubility.

DETAILED DESCRIPTION OF THE EMBODIMENTS

Hereunder the embodiments of the present invention will be detailly described. It should be understood that the embodiments described here are only provided to describe and explain the present invention, but shall not be deemed as constituting any limitation to the present invention.

In the present invention, a dendritic polymer is also known as a dendronized polymer, which is a linear polymer with a dendron in each repeating unit.

The dendritic polymer in the present invention has a structure denoted by Z-(Q)n-Y, wherein Z represents a group that can have condensation reaction with acyl halides, Q represents a dendritic constitutional repeating unit of the dendritic polymer; n represents the generation number of the dendritic polymer, and is an integer within a range of 2-6; and Y represents a group containing $SO_3^-$ and $COO^-$.

Herein the group that can have condensation reaction with acyl halide can be any known group that can have condensation reaction with acyl halides in the art, and preferably Z is —OH or —$NH_2$.

In the above formula, Q can be any dendritic structural unit; a dendritic structural unit or dendritic repeating unit is a structural unit or repeating unit that has the above-mentioned dendritic structure; for example, the following structure can be deemed as having a dendritic shape, or can further create a dendritic shape with a NHX group.

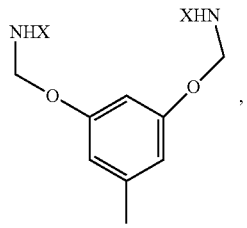

According to the present invention, preferably the dendritic polymer in the present invention has a structure in which Q has a structure denoted by the following formula (I) and Y has a structure denoted by the following formula (II),

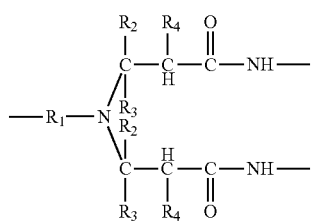

formula (I)

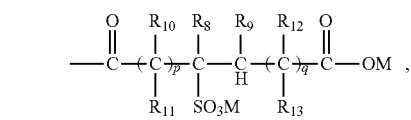

formula (II)

in formula (I), $R_1$ represents $C_1$-$C_5$ alkylene; $R_2$-$R_4$ can be identical to or different from each other, and are H or $C_1$-$C_5$ alkyl respectively; in addition, for n structures denoted by formula (I), $R_1$-$R_4$ can be identical to or different from each other;

in formula (II), $R_8$-$R_{13}$ can be identical to or different from each other, and are H or $C_1$-$C_5$ alkyl respectively; p and q can be identical to or different from each other, and are an integer within a range of 0-5 respectively; and M is H, Na, or K.

In the present invention, the alkyl can be n-alkyl (linear alkyl) or iso-alkyl (branched alkyl).

In the present invention, the alkylene can be n-alkylene (linear alkylene) or iso-alkylene (branched alkylene).

In the present invention, for example, the $C_1$-$C_5$ alkylene can be methylene, ethylidene (—$CH_2CH_2$—), propylidene (—$CH_2CH_2CH_2$—), iso-propylidene (—$CH(CH_3)CH_2$— or —$CH_2CH(CH_3)$—), butylidene (—$CH_2CH_2CH_2CH_2$—) or any of its isomers, or amylidene (—$CH_2CH_2CH_2CH_2CH_2$—) or any of its isomers. Preferably it is ethylidene in the present invention.

In the present invention, the $C_1$-$C_5$ alkyl can be methyl, ethyl, n-propyl, isopropyl, n-butyl, isobutyl, tertiary butyl, n-pentyl, or neo-pentyl. Preferably it is methyl and/or ethyl.

In the present invention, preferably the dendritic polymer has a structure denoted by the following formula (III) and/or formula (IV),

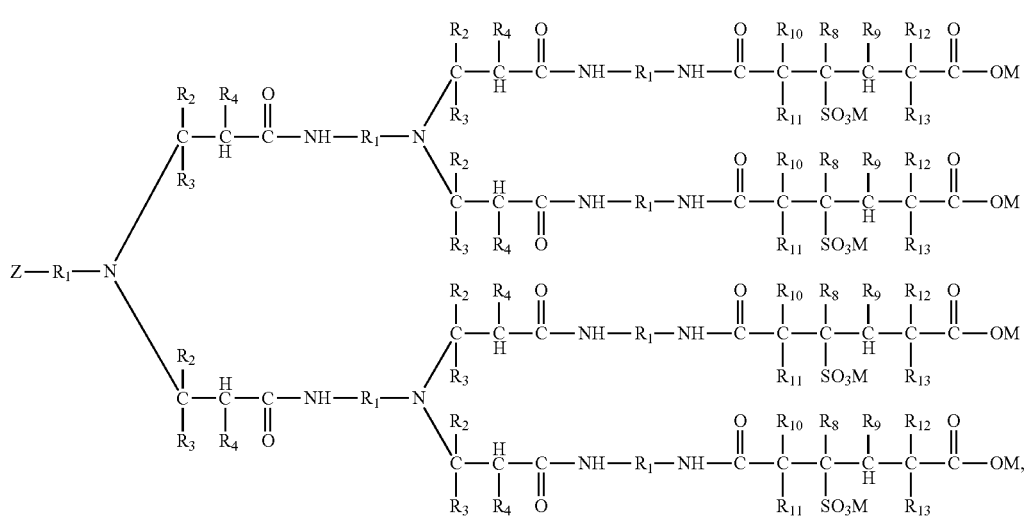

formula (III)

-continued

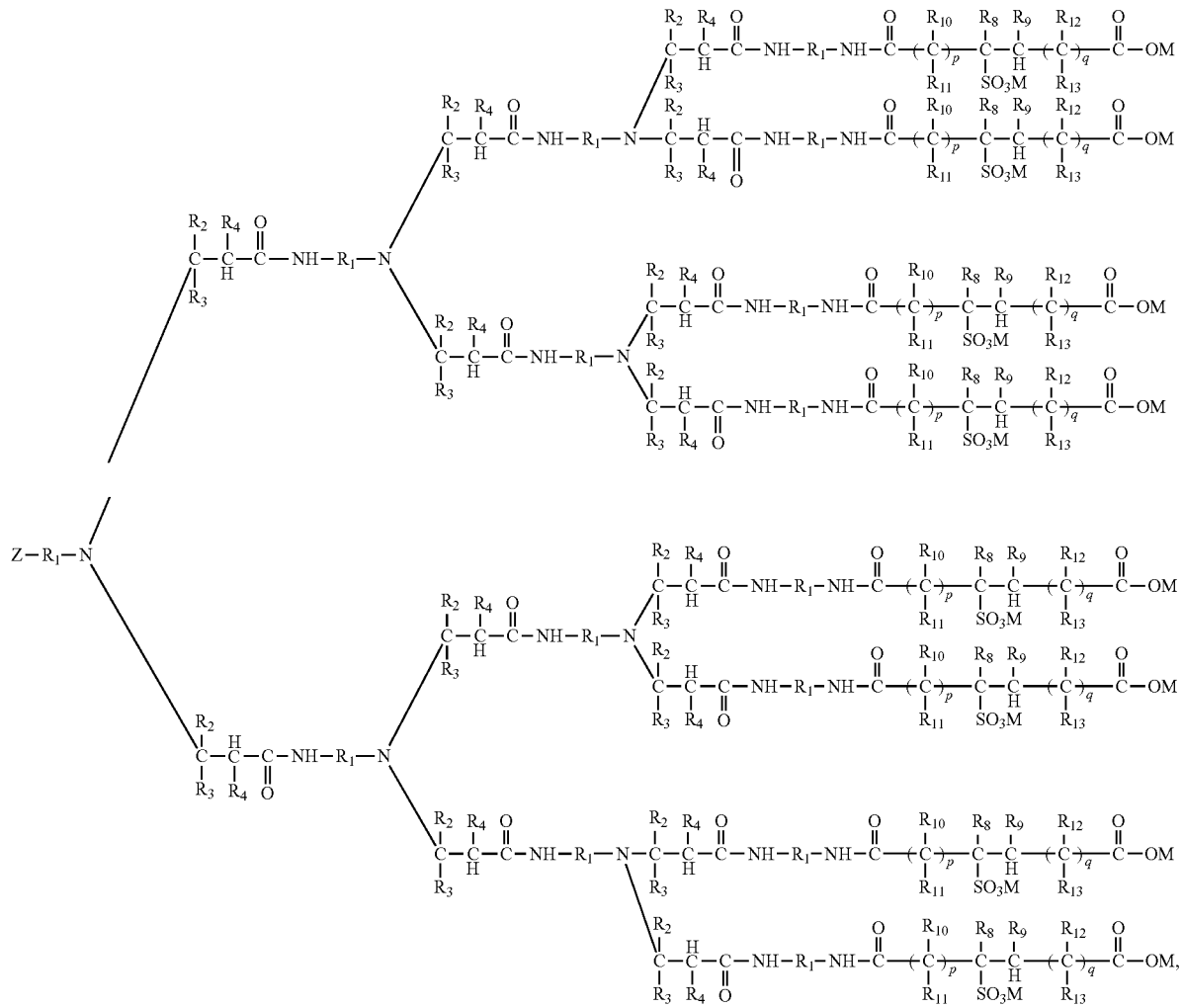

formula (IV)

Z, $R_1$-$R_4$, $R_8$-$R_{13}$, M, p, and q are in the same definitions as those described above.

Wherein the polymer denoted by formula (III) is a 2G dendritic polymer, i.e. its generation number n is 2; the polymer denoted by formula (IV) is a 3G dendritic polymer, i.e. its generation number n is 3. The polymer denoted by formula (III) and the polymer denoted by formula (IV) may be different from each other in terms of the generation number only, or may be different from each other in terms of Z, $R_1$-$R_{13}$, M, p, and q.

The dendritic polymer in the present invention, wherein preferably Z is OH; $R_1$ is $CH_2CH_2$; $R_2$-$R_{13}$ are H respectively; M is Na or K; and both p and q are 0 or 1.

The dendritic polymer monomer provided in the present invention has a structure denoted by Z'-(Q)n-Y, wherein Z' represents a structure denoted by the following formula (a) and/or formula (b); Q represents a dendritic constitutional repeating unit of the dendritic polymer monomer; n represents the generation number of the dendritic polymer monomer, and is an integer within a range of 2-6; and Y represents a group containing $SO_3^-$ and $COO^-$,

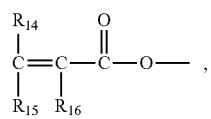

formula (a)

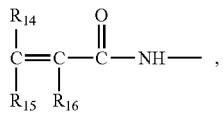

formula (b)

$R_{14}$-$R_{16}$ are identical to or different from each other, and are H or $C_1$-$C_5$ alkyl respectively.

The dendritic polymer monomer provided in the present invention, wherein Q can be any dendritic structural unit of the dendritic polymer monomer, and preferably has a structure denoted by the following formula (I), and Y has a structure denoted by the following formula (II),

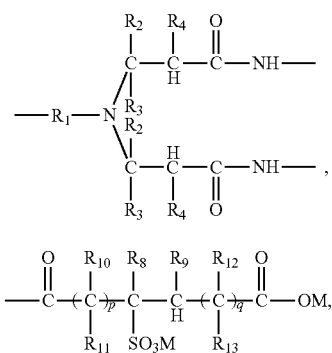

formula (I)

formula (II)

Wherein in formula (I), $R_1$ represents $C_1$-$C_5$ alkylene, $R_2$-$R_4$ can be identical to or different from each other, and are H or $C_1$-$C_5$ alkyl respectively; in addition, for n structures denoted by formula (I) $R_1$-$R_4$ can be identical to or different from each other;

in formula (II), $R_8$-$R_{13}$ can be identical to or different from each other, and are H or $C_1$-$C_5$ alkyl respectively; p and q can be identical to or different from each other, and are an integer within a range of 0-5 respectively; and M is H, Na, or K.

In the present invention, preferably the dendritic polymer monomer has a structure denoted by any of the following formula (1), (2), (3) and (4),

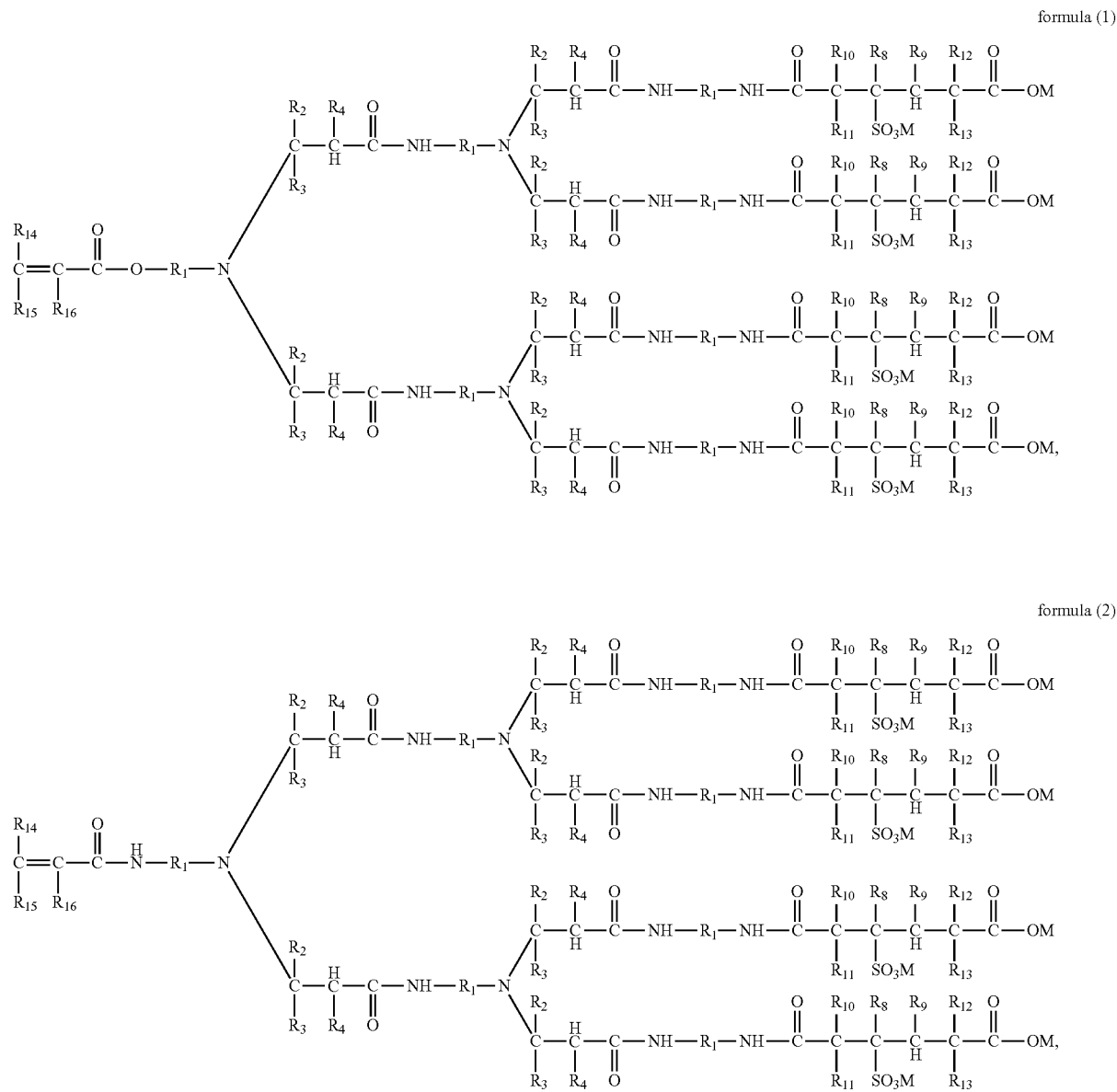

formula (1)

formula (2)

-continued
formula (3)
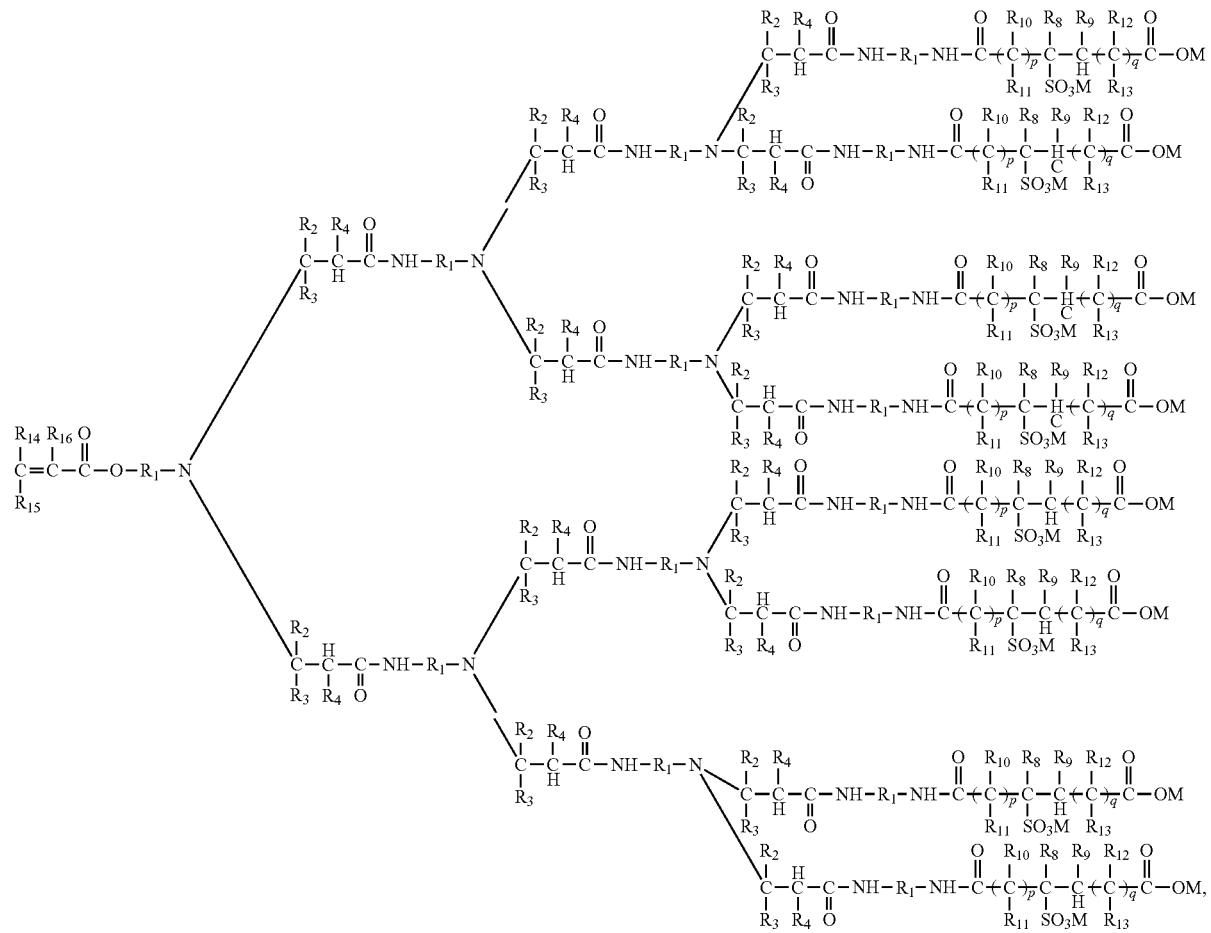
formula (4)
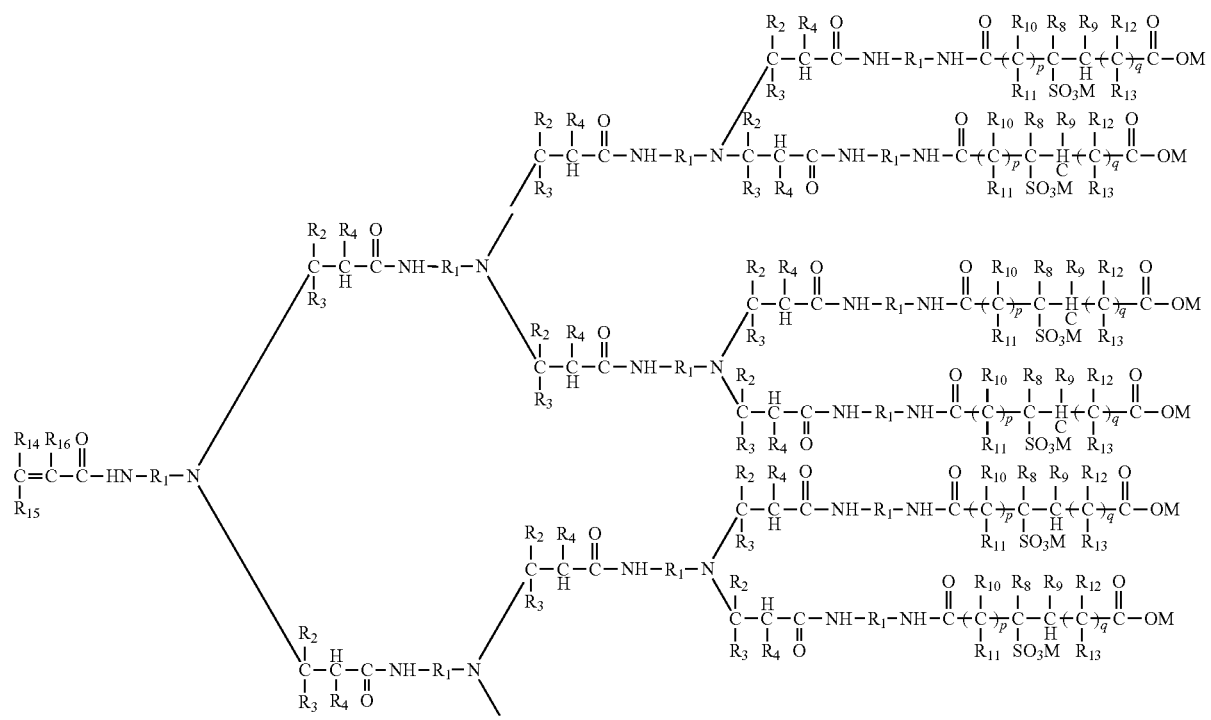

-continued

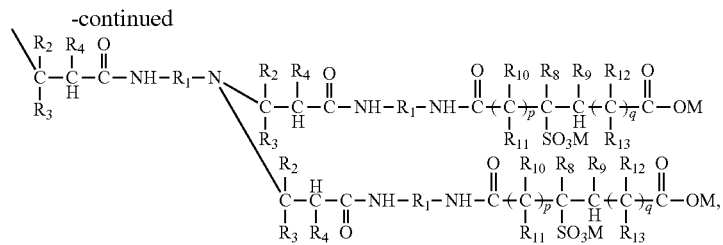

$R_1$-$R_4$, $R_8$-$R_{16}$, M, p, and q are in the same definitions as those in the dendritic polymer described above.

In the present invention, wherein more preferably the dendritic polymer monomer has a structure denoted by the above formula (1) and/or formula (3), and, in formula (1) and formula (3), $R_1$ is $CH_2CH_2$; $R_2$-$R_4$ and $R_8$-$R_{16}$ are H; M is Na or K; and both p and q are 0 or 1.

According to a method for preparation of a dendritic polymer provided in the present invention, the method comprises the following steps if the dendritic polymer has a structure denoted by the above formula (III) and/or formula (IV):

(1) preparing an intermediate of a structure denoted by the following formula (5) and/or formula (6), formula (5)

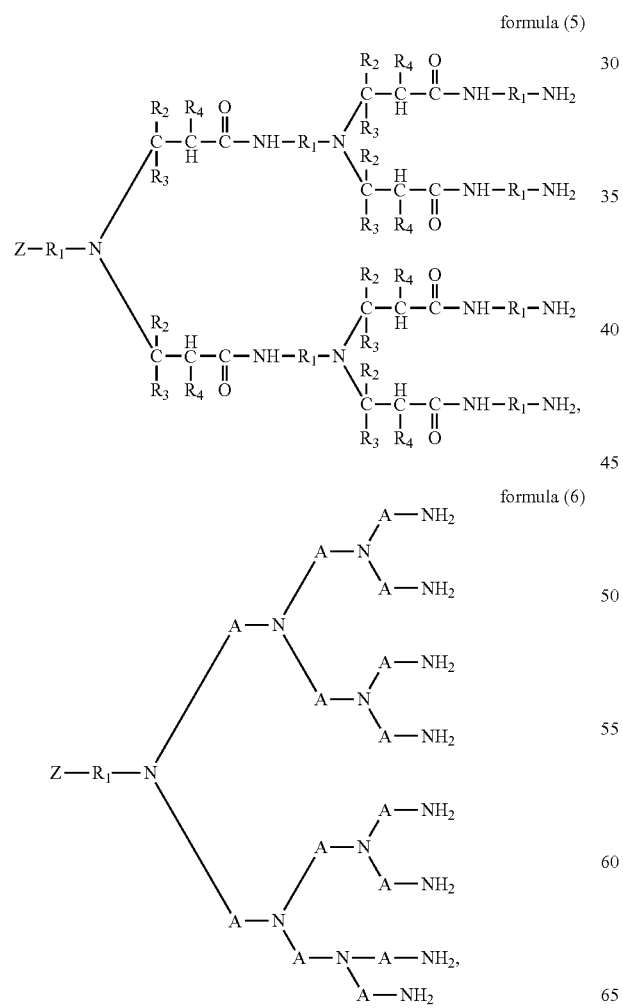

formula (6)

in formula (6), A is

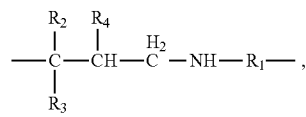

in formula (5) and formula (6), Z represents a group which can have condensation reaction with acyl halide, preferably Z is OH or $NH_2$; $R_1$ represents $C_1$-$C_5$ alkylene, $R_2$-$R_4$ can be identical to or different from each other, and are H or $C_1$-$C_5$ alkyl respectively; in addition, for n structures denoted by formula (I), $R_1$-$R_4$ can be identical to or different from each other;

(2) under nucleophilic addition reaction conditions, controlling the intermediate to contact with an unsaturated anhydride denoted by the following formula (7), to form carboxylic acid amide that contains unsaturated bonds, formula (7)

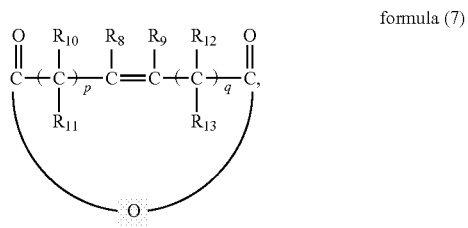

in formula (7), $R_8$-$R_{13}$ can be identical to or different from each other, and are H or $C_1$-$C_5$ alkyl respectively; p and q can be identical to or different from each other, and are an integer within a range of 0-5 respectively;

(3) at 30-100° C. reaction temperature, controlling the carboxylic acid amide that contains unsaturated bonds obtained in step (2) to contact with sulfurous acid and/or an alkali metal sulphite. The intermediate in the structure denoted by formula (5) and/or formula (6) can be prepared with a known method in the art; for example, the intermediate in the structure denoted by formula (5) can be obtained by controlling an unsaturated acid alkyl ester to have Michael addition reaction with the amine in Z—$R_1$—$NH_2$, then controlling the product of the Michael addition reaction to have condensation reaction with the alkyl diamine in $NH_2$—$R_1$—$NH_2$, and then controlling the product of the condensation reaction to have the Michael addition reaction and condensation reaction described above repeatedly in sequence to obtain a polymer intermediate in a dendritic structure, the number of repetitions corresponds to the required generation number.

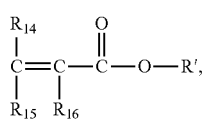

wherein Z, $R_1$, $R_{14}$-$R_{16}$ are in the same definitions as those described above, R' is preferably $C_1$-$C_5$ alkyl, more preferably methyl or ethyl.

The Michael addition reaction preferably happens in the existence of a solvent, which is preferably one or more of methanol, ethanol, isopropanol, and tert-butyl alcohol.

The conditions of the Michael addition reaction can include: 25-55° C. reaction temperature, and 3-7 h reaction time, preferably 4-6 h reaction time.

The condensation reaction preferably happens in the existence of a solvent, which is preferably one or more of methanol, ethanol, isopropanol, and tert-butyl alcohol.

The conditions of the condensation reaction can include: 10-60° C. reaction temperature, and 20-35 h reaction time, preferably 24-30 h reaction time.

Hereunder the preparation of an intermediate will be described in an example of the intermediate denoted by formula (5d).

formula (5d)

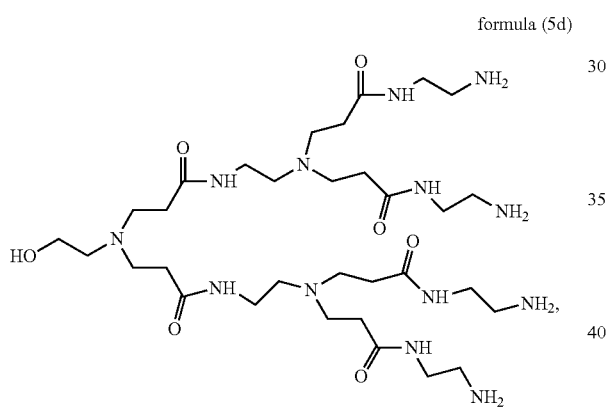

According to a preferred embodiment of the present invention, the intermediate denoted by formula (5d) can be prepared with a method that comprises the following steps:
(I) adding methyl acrylate, ethanolamine, and a solvent (e.g., methanol) into a reactor, stirring for 10-60 min while filling a shielding gas (e.g., $N_2$) into the reactor at 10-25° C., and then heating up to 30-40° C. and keeping for 3-7 h at that temperature, and carrying out reduced pressure distillation to remove the organic solvent, so as to obtain a product in the structure denoted by formula (5a);
(II) loading the product in the structure denoted by formula (5a) and an organic solvent (e.g., methanol) into a reactor, adding ethylene diamine in droplets while stirring at 10-40° C., controlling the reactants to react for 20-35 h at that temperature, and then carrying out reduced pressure distillation to remove the organic solvent, so as to obtain an intermediate product in the structure denoted by formula (5b);
(III) loading the intermediate product in the structure denoted by formula (5b) and an organic solvent (e.g., methanol) into a reactor, adding methyl acrylate in droplets while stirring at 10-40° C., controlling the reactants to react for 20-35 h at that temperature, and then carrying out reduced pressure distillation to remove the organic solvent, so as to obtain an intermediate product in the structure denoted by formula (5c);
(IV) loading the intermediate product in the structure denoted by formula (5c) and an organic solvent (e.g., methanol) into a reactor, adding ethylene diamine in droplets while stirring at 10-40° C., controlling the reactants to react for 20-35 h at that temperature, and then carrying out reduced pressure distillation to remove the methanol, so as to obtain an intermediate product in the structure denoted by formula (5d).

formula (5a)

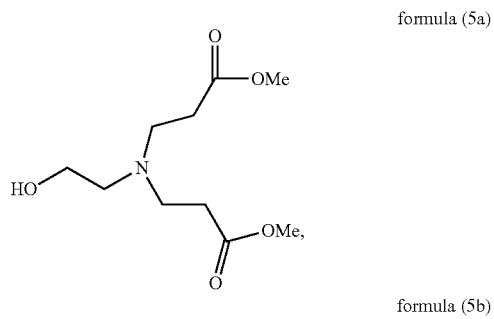

formula (5b)

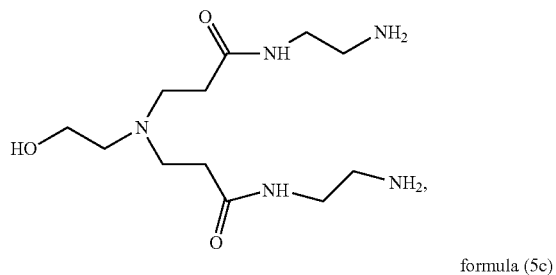

formula (5c)

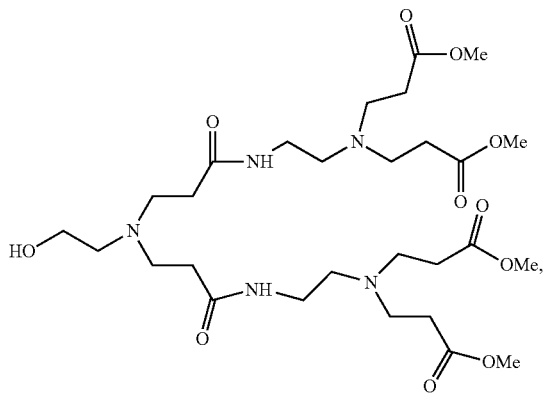

The above step (III) and step (IV) can be repeated to evolve a generation, so as to obtain an intermediate in the structure denoted by formula (6).

In formula (5) and formula (6), if $R_1$-$R_4$ are other substituents, the intermediate can be prepared similarly with the method described above, provided that appropriate raw materials are selected.

According to the preparation method provided in the present invention, if the solvents used in the steps are the same, the next step of reaction can be executed directly without removing the solvent.

In step (2), the unsaturated anhydride can be denoted by the following structural formula:

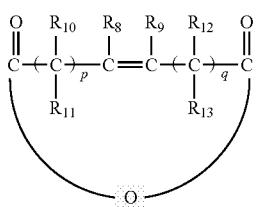

Wherein $R_8$-$R_{13}$, p and q are in the same definitions as those described above.

Preferably, the unsaturated anhydride is maleic anhydride.

The conditions of the nucleophilic addition reaction in step (2) include: 60-100° C. reaction temperature, preferably 80° C., and 4-20 h reaction time.

The step (2) is executed preferably under stirring condition, more preferably in the existence of an organic solvent such as an amide solvent and/or haloalkane solvent, further more preferably in the existence of one or more of N,N-dimethyl formamide, N,N-dimethyl acetamide, dichloromethane, trichloromethane, dichloroethane, and methyl benzene. The unsaturated anhydride is preferably added in droplets.

The reaction in step (3) happens preferably in the existence of a solvent, which is preferably an amide solvent and/or haloalkane solvent, more preferably is one or more of N,N-dimethyl formamide, N,N-dimethyl acetamide, dichloromethane, trichloromethane, dichloroethane, and methyl benzene. The organic solvent in step (2) can be identical to or different from the organic solvent in step (3); preferably the organic solvent in step (2) is identical to the organic solvent in step (3). More preferably, the reaction product in step (2) is directly used in the reaction in step (3) without separation.

The conditions of the contact reaction in step (3) can include: 30-70° C. reaction temperature and 3-20 h reaction time. The reaction time can be determined by judging the time when the double bonds have disappeared completely. Whether the double bonds have disappeared completely can be judged by means of bromide addition (please see chemical books for details, or with the method for determining free acrylic acid or bromine value as described in GB/T10533-2000 "Water Treatment Chemicals—Polyacrylic Acid" or GB/T10535-1997 "Water Treatment Chemicals—Hydrolyzed Polymaleic Anhydride". In the embodiments of the present invention, whether the double bonds have disappeared completely is judged with the method for determining free acrylic acid or bromine value as described in GB/T10533-2000 "Water Treatment Chemicals—Polyacrylic Acid").

After the reaction in step (3) is completed, the obtained mixture is filtered and the organic solvent is distilled off; then active carbon is added to make adsorption treatment for 14-28 h to remove impurities; then the active carbon is filtered off, and the obtained solution is dehydrated in vacuum, to obtain the target dendritic polymer.

The method for preparation of a dendritic polymer monomer provided in the present invention comprises preparing a dendritic polymer with the method described above, and then controlling the dendritic polymer to contact with an unsaturated acyl halide under the conditions of condensation reaction.

The contact reaction between the dendritic polymer and the unsaturated acyl halide preferably happens in the existence of a solvent, and the contact conditions can include: 0-20° C. reaction temperature and 0.5-10 h reaction time.

According to a preferred embodiment of the present invention, the method for preparation of a dendritic polymer monomer can comprise the following steps: loading the dendritic polymer, an organic solvent, and an acid binding agent into a reaction bulb equipped with a cooling device, cooling the mixture down to about 5° C., adding an unsaturated acyl halide slowly (the temperature is controlled to be not higher than 15° C. in the adding process), and then keeping the reaction for 0.5-8 h at about 10° C.; keeping the reactants in still state to separate the organic phase, neutralizing and washing with saturated sodium bicarbonate solution for several times, drying with anhydrous sodium sulfate, and distilling off the organic solvent to obtain a crude product, and then purifying the crude product to obtain polymerized product, i.e., the expected dendritic polymer monomer.

The unsaturated acyl halide can be unsaturated acyl chloride and/or unsaturated acyl bromide, and preferably the molecule of the unsaturated acyl halide contains 3-6 carbon atoms; particularly, in the present invention, the unsaturation acyl halide is acryloyl chloride and/or methacrylic chloride.

The acid binding agent can be any alkaline substance, preferably is an organic nitrogen containing compound, more preferably is one or more of methylamine, ethylamine, propylamine, dimethylamine, diethylamine, triethylamine, tri-n-propylamine, tri-n-butylamine, and pyridine.

The mole ratio of the dendritic polymer:organic solvent: acid binding agent:unsaturated acyl halide is preferably 1:18-22:1.0-1.1:1.0-1.05.

Since all the reactions involved in the preparation method described above are ordinary organic chemical reactions and the direction of each reaction is deterministic and unique, the progress of the reactions can be determined according to the raw materials and conditions of the reactions, without characterizing the products separately. Of course, the synthesis of intermediate products, intermediates, and target products can be determined by conventional means, such as infrared detection, nuclear magnetic resonance detection, or mass spectrometric detection, etc.

Also, the present invention discloses an application of the dendritic polymer and dendritic polymer monomer in preparation of filtrate reducers for drilling fluids, oil-displacing agents, thickening agents for fracturing liquids, and oil field water treatment agents.

In the hyperbranched copolymer provided in the present invention, the total weight of the dendritic structural unit A, amphoteric ion structural unit B, structural unit C, and structural unit D accounts for 90% or more in the total weight of the hyperbranched polymer.

More preferably, the dendritic structural unit A has a structure denoted by any of the following formula (A1), (A2), (A3), and (A4), formula (A1)
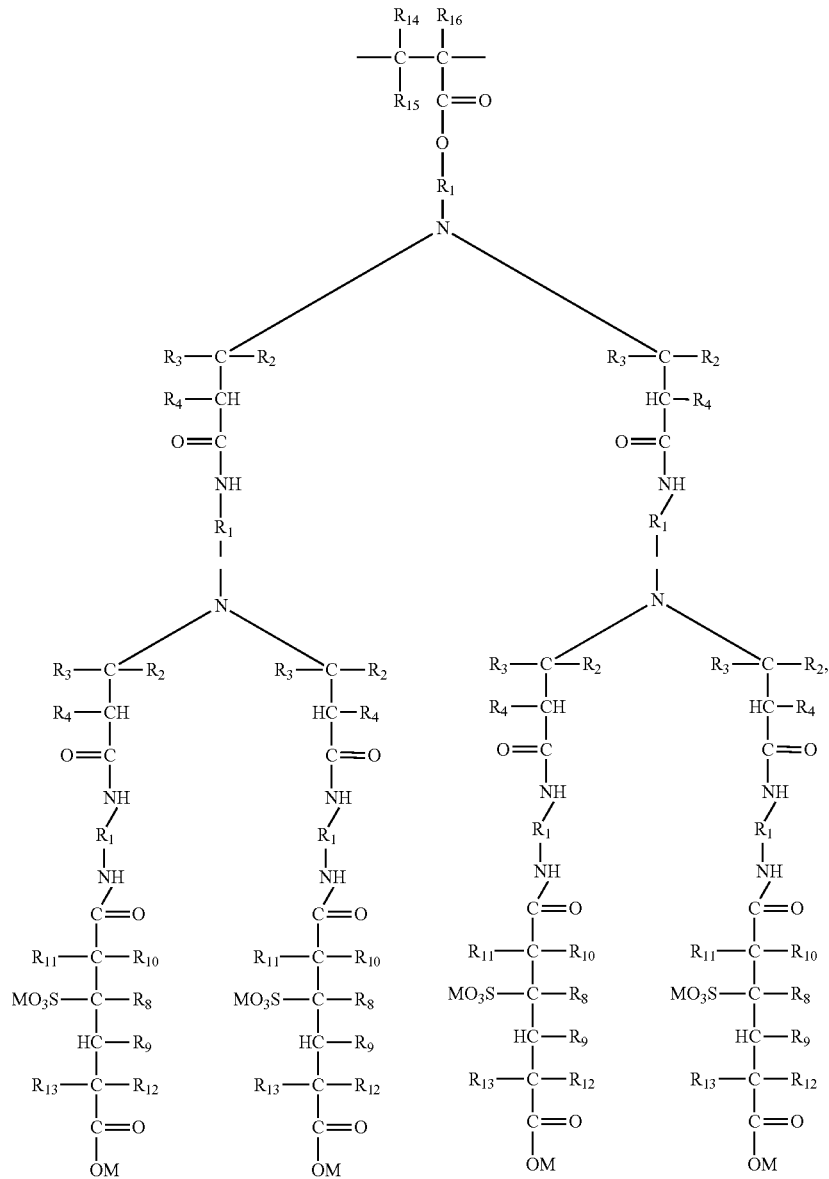

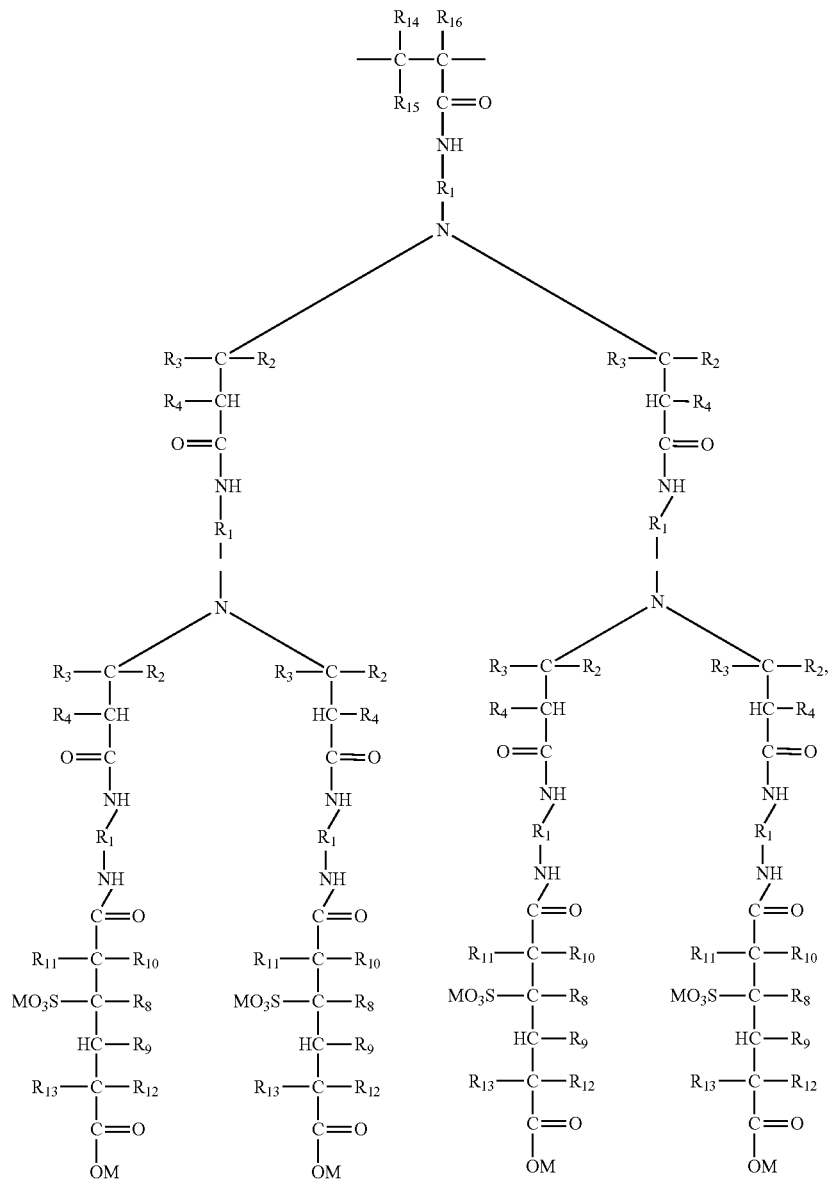
formula (A2)

formula (A3)
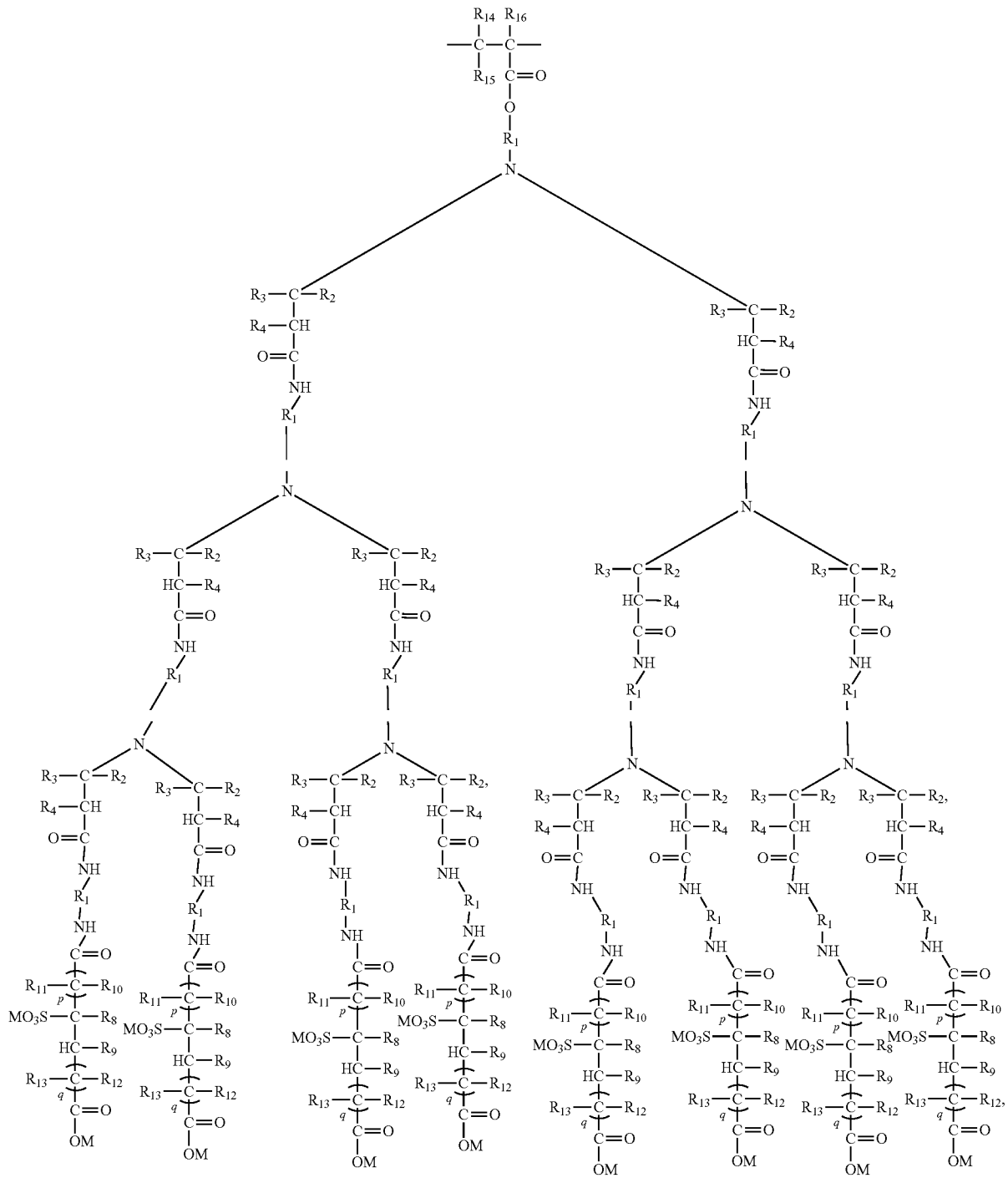

formula (A4)

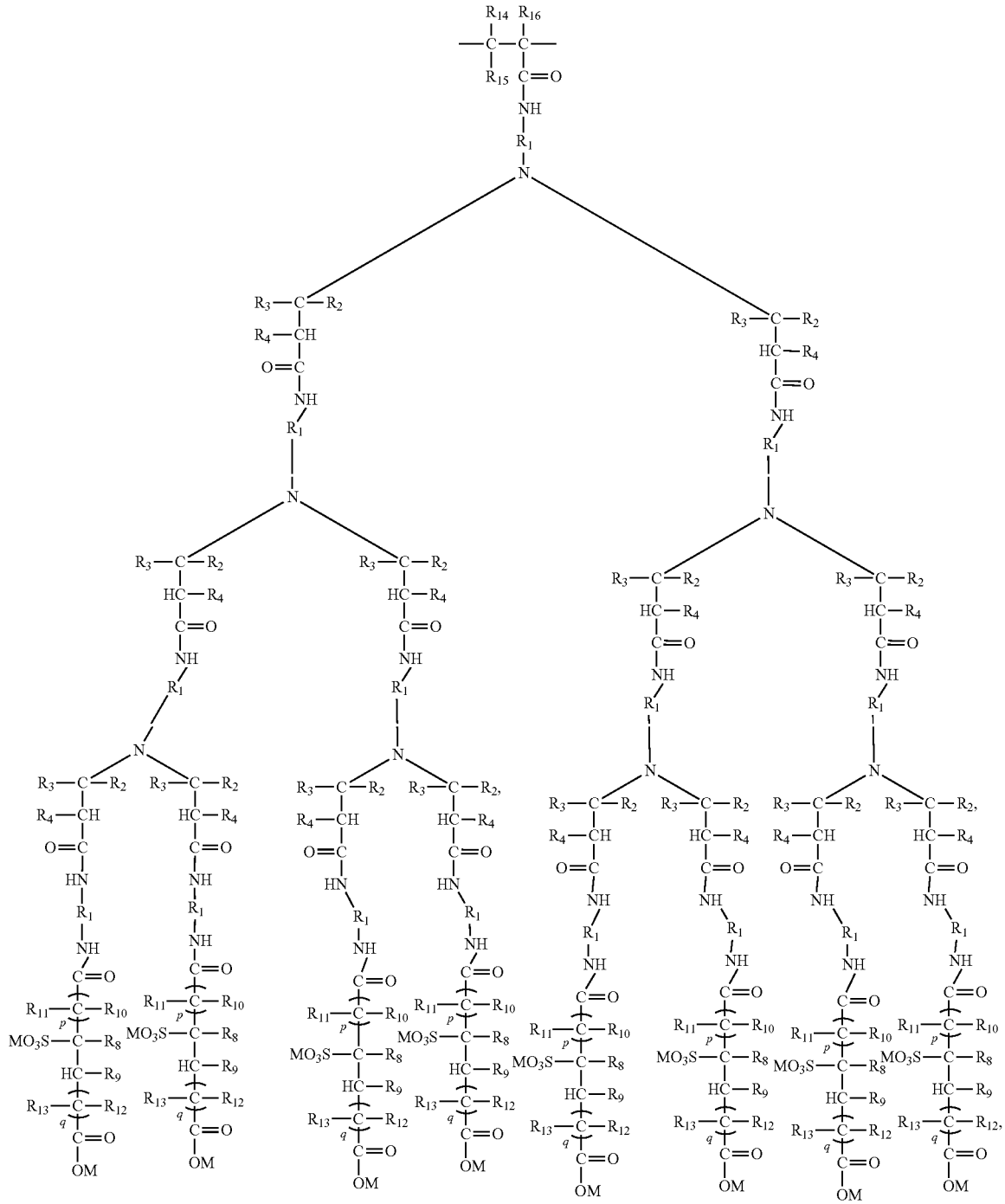

$R_1$-$R_4$, $R_8$-$R_{16}$, M, p and q are in the same definitions are those described above.

More preferably, the dendritic structural unit A has a structure denoted by formula (1) and/or formula (3), and, in formula (1) and formula (3), $R_1$ is $CH_2CH_2$; $R_2$-$R_4$ and $R_8$-$R_{16}$ are H respectively; M is Na; and both p and q are 0.

According to the present invention, the $X^-$ in the amphoteric ion structural unit B can be any halogen anion, such as $Cl^-$, $Bf^-$, or $F^-$, and can be the same or different among different structural units of the same polymer.

The hydroxy-substituted $C_1$-$C_3$ alkyl can be —CH(OH)$CH_3$, —CH(OH)$C_2H_5$, or —CH(OH)$C_3H_7$, for example.

In the hyperbranched copolymer in the present invention, the amphoteric ion structural unit B is one or more of the structures denoted by the following formulae,

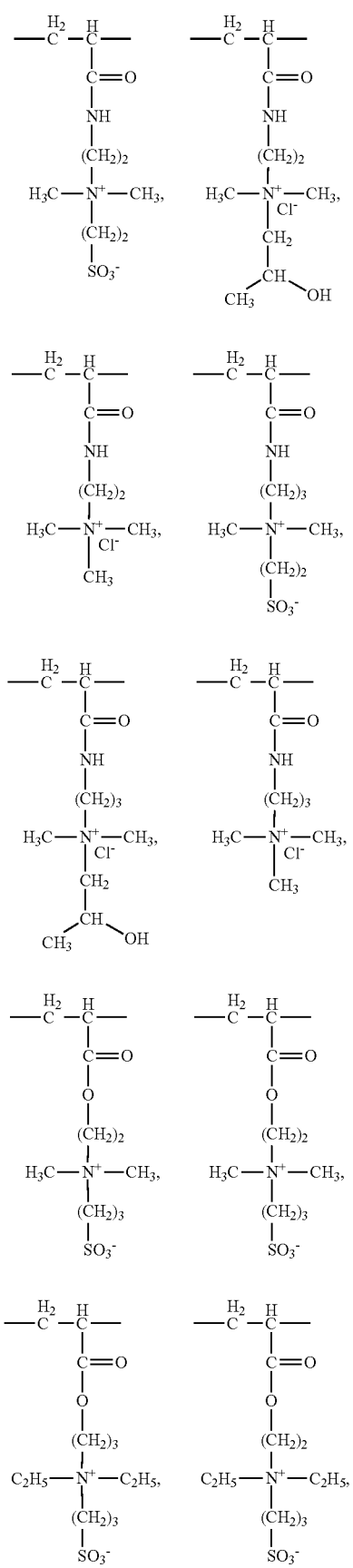

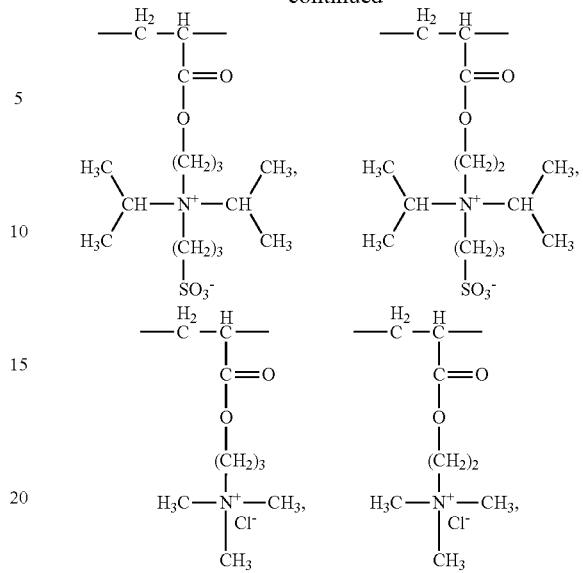

According to the present invention, the structural unit C can be in the structure denoted by formula (C) in which $R_6$ is H, methyl, ethyl or propyl and $R_7$ and $R_8$ are H respectively, or $R_8$ is H, methyl, ethyl or propyl and $R_7$ and $R_6$ are H respectively; preferably, the structural unit C is in the structure denoted by formula (C) in which $R_8$ is H or methyl and $R_7$ and $R_6$ are H respectively (i.e, an acrylamide structural unit or a methyl acrylamide structural unit).

In the hyperbranched copolymer in the present invention, preferably the structural unit D is in a structure denoted by at least one of the following structural formulae,

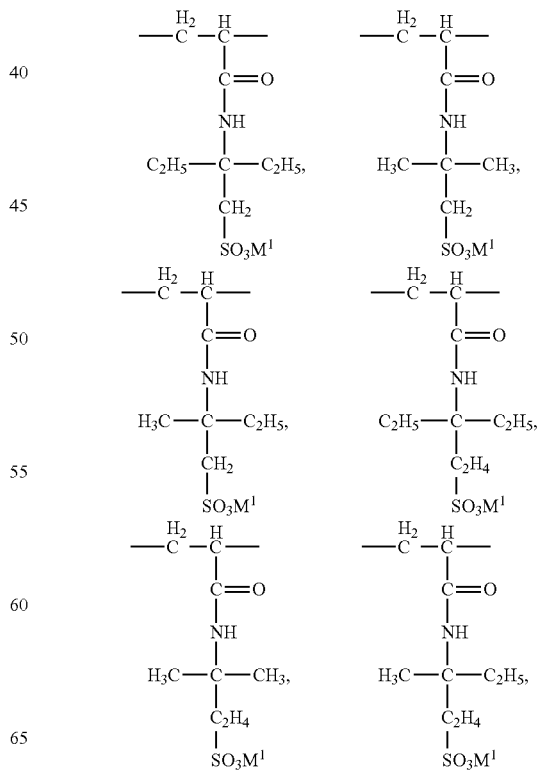

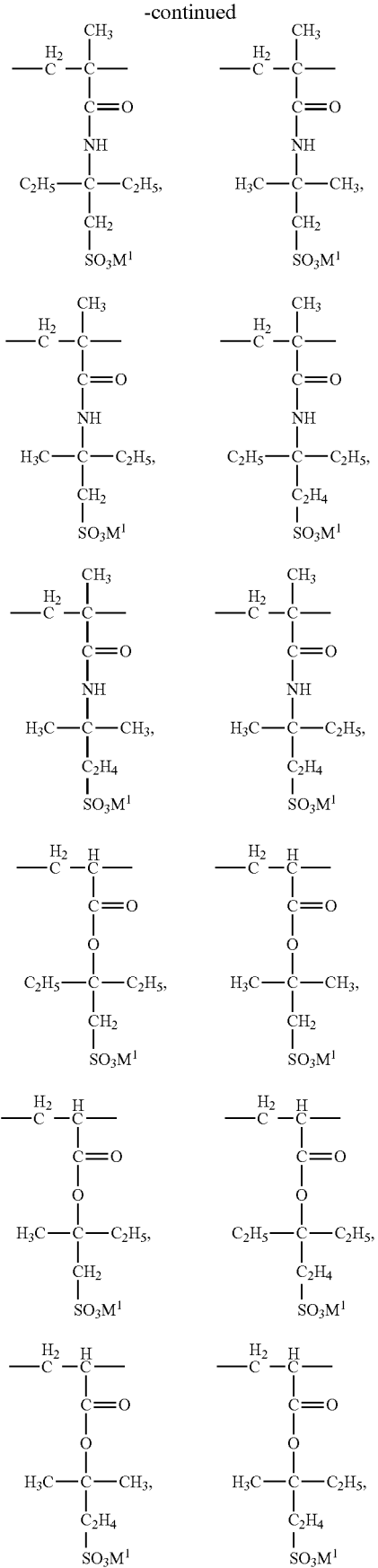
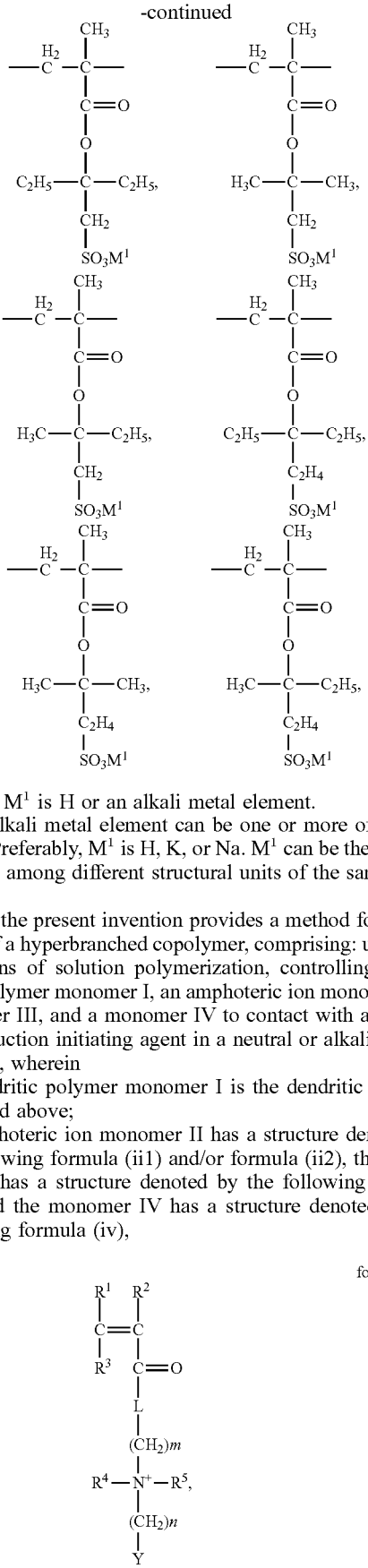

wherein $M^1$ is H or an alkali metal element.

The alkali metal element can be one or more of Li, Na, and K. Preferably, $M^1$ is H, K, or Na. $M^1$ can be the same or different among different structural units of the same polymer.

Also, the present invention provides a method for preparation of a hyperbranched copolymer, comprising: under the conditions of solution polymerization, controlling a dendritic polymer monomer I, an amphoteric ion monomer II, a monomer III, and a monomer IV to contact with an oxidation-reduction initiating agent in a neutral or alkaline environment, wherein the dendritic polymer monomer I is the dendritic polymer described above;

the amphoteric ion monomer II has a structure denoted by the following formula (ii1) and/or formula (ii2), the monomer III has a structure denoted by the following formula (iii), and the monomer IV has a structure denoted by the following formula (iv),

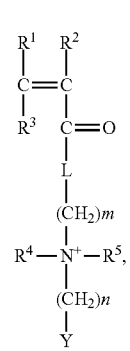

formula (ii1)

-continued formula (ii2)
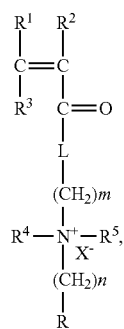

formula (iii)
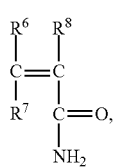

formula (iv)
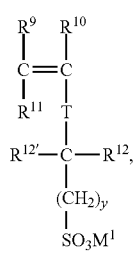

in formula (ii1) and formula (ii2), $R^1$, $R^2$, $R^3$, $R^4$ and $R^5$ are H or $C_1$-$C_3$ alkyl or iso-alkyl respectively, m and n are an integer within a range of 0-5 respectively, and L is O or NH; in formula (ii1), Y is $COO^-$ or $SO_3^-$; in formula (ii2), $X^-$ is halogen anion, and R is H or hydroxyl-substituted $C_1$-$C_3$ alkyl, in formula (iii), $R^6$, $R^7$ and $R^8$ are H or $C_1$-$C_3$ alkyl respectively, in formula (iv), $R^9$, $R^{10}$, $R^{11}$, and $R^{12'}$ are H or $C_1$-$C_3$ alkyl; $R^{12}$ is a bond or $C_1$-$C_{12}$ linear or branched alkylene; T is a bond or

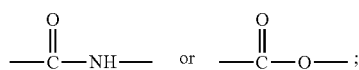

$M^1$ is H or an alkali metal element; and y is an integer within a range of 1-4;

in addition, calculated in moles, the ratio of dendritic polymer monomer I:amphoteric ion monomer II:monomer III:monomer IV is 0.03-0.35:0.03-0.5:0.03-0.3:0.15-0.95, and the contact conditions are determined in a way that the apparent viscosity of 1 mass % water solution of the obtained polymer is 20-60 mPa·s.

Preferably, Q is in a structure denoted by the following formula (I), and Y is in a structure denoted by the following formula (II), formula (I)
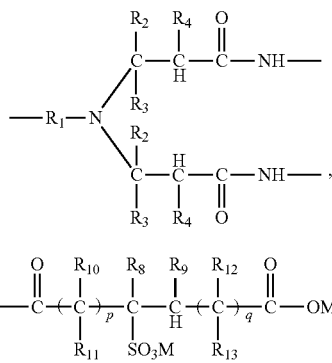

formula (II)
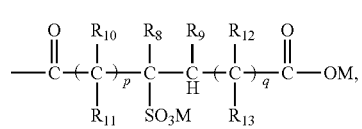

Wherein in formula (I), $R_1$ represents $C_1$-$C_5$ alkylene, $R_2$-$R_4$ can be identical to or different from each other, and are H or $C_1$-$C_5$ alkyl respectively; in addition, for n structures denoted by formula (I), $R_1$-$R_4$ can be identical to or different from each other;

in formula (II), $R_8$-$R_{13}$ can be identical to or different from each other, and are H or $C_1$-$C_5$ alkyl respectively; p and q can be identical to or different from each other, and are an integer within a range of 0-5 respectively; and M is H, Na, or K.

More preferably, the dendritic polymer monomer I has a structure denoted by any of the formula (A1), (A2), (A3), and (A4) as described above.

According to the preparation method disclosed in the present invention, wherein the dendritic polymer monomer I has a structure denoted by formula (1) and/or formula (3), and, in formula (1) and formula (3), $R_1$ is $CH_2CH_2$; $R_2$-$R_4$ and $R_8$-$R_{13}$ are H respectively; M is Na; and both p and q are 0.

In the present invention, preferably the amphoteric ion monomer II is one or more of the structures denoted by the following formulae,

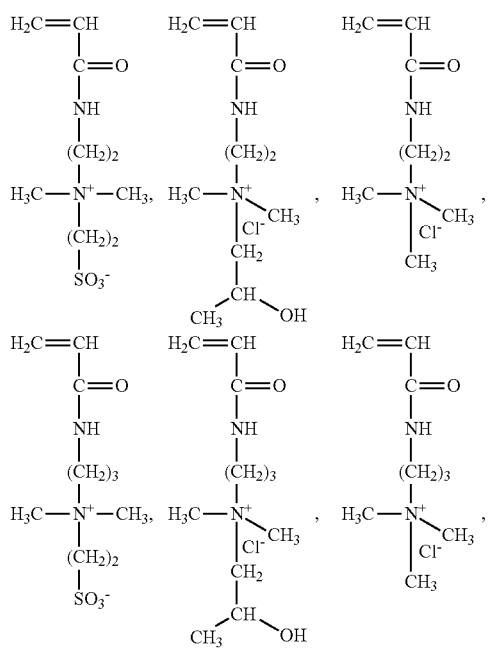

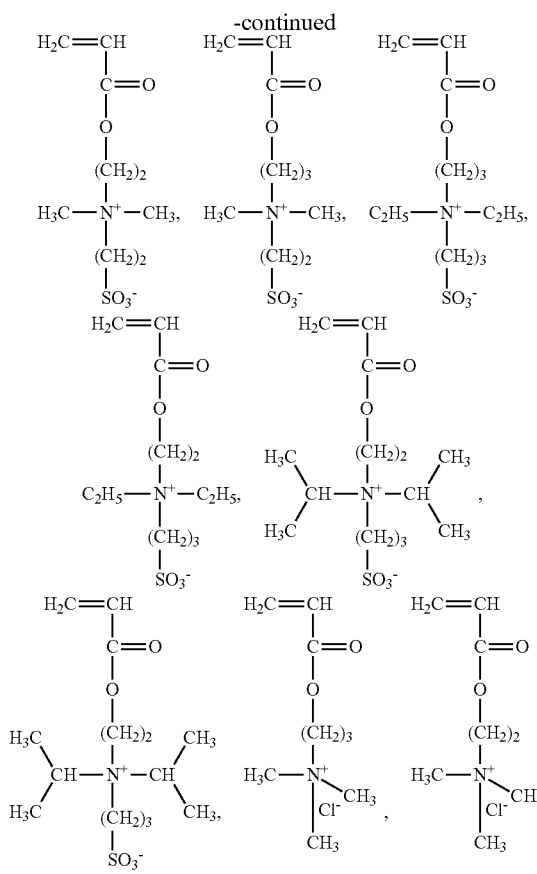

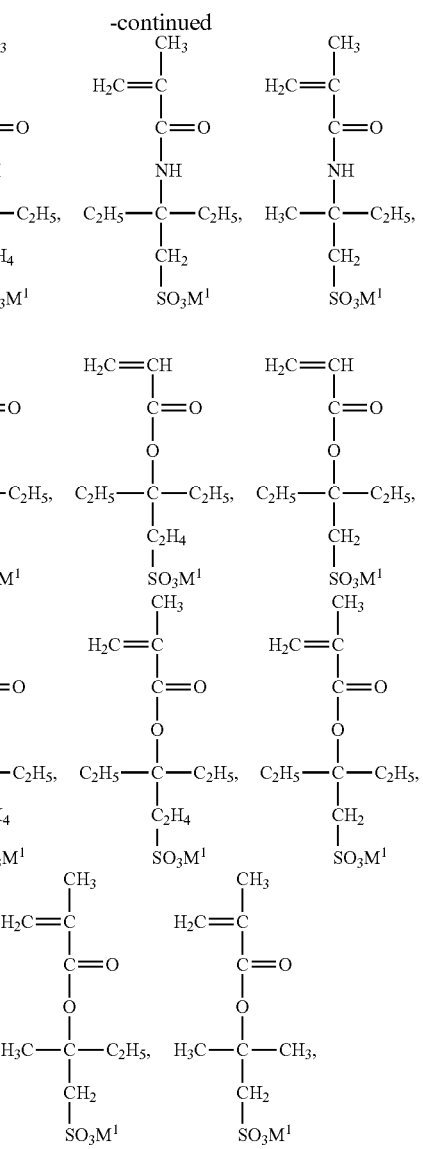

More preferably, the amphoteric ion monomer II is one or more selected from the group consisting of 3-acrylamide propyl dimethyl ammonium propylsulfonate, 3-acrylamide propyl (2-hydroxy)-propyl dimethyl ammonium chloride, 3-acryloxy ethyl dimethyl ammonium propylsulfonate, 3-acryloxy ethyl diethyl ammonium propylsulfonate, 3-acryloxy ethyl diisopropyl ammonium propylsulfonate, 3-acrylamide propyl trimethyl ammonium chloride, and 3-acryloxy propyl trimethyl ammonium chloride.

According to the present invention, the monomer III can be in the structure denoted by formula (iii) in which $R_6$ is H, methyl, ethyl or propyl, and $R_7$ and $R_8$ are H respectively, or $R_8$ is H, methyl, ethyl or propyl and $R_7$ and $R_6$ are H respectively; more preferably, the monomer III is in the structure denoted by formula (iii) in which $R_8$ is H or methyl and $R_7$ and $R_6$ are H respectively (i.e., acrylamide or methyl acrylamide).

According to a method for preparation of a hyperbranched polymer disclosed in the present invention, the monomer IV is in a structure denoted by at least one of the following structural formulae,

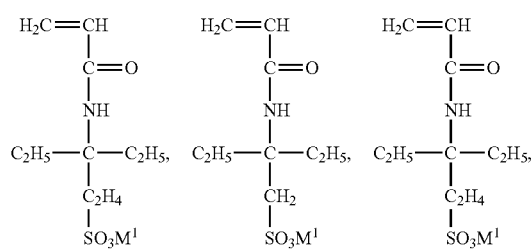

wherein $M^1$ is H or an alkali metal element. The alkali metal element can be one or more of Li, Na, and K.

According to the preparation method disclosed in the present invention, wherein the solution polymerization conditions include: initial temperature of polymerization can be 20-80° C., preferably 30-60° C.; polymerization reaction time can be 20-100 min, preferably 30-90 min.

In the present invention, the pH value of the neutral or alkaline environment is preferably 7-10.

The neutral or alkaline environment can be obtained with 10-20 wt % sodium hydroxide and/or potassium hydroxide solution.

Preferably the solvent used in solution polymerization is water. More preferably, in relation to 0.05-0.25 mole dendritic polymer monomer, the usage of water is 95-200 ml, and the usage of the oxidation-reduction initiating agent is 0.2-1.2 g.

The oxidation-reduction initiating agent can be any known oxidation-reduction initiating agent in the domain of polymers; preferably, in the oxidation-reduction initiating agent, the oxidizing agent is potassium persulfate and/or ammonium persulfate, and the reducing agent is one of sodium bisulfite, sodium pyrosulfite, sodium sulfite, and sodium thiosulfate.

Preferably, the method for preparation of a hyperbranched polymer disclosed in the present invention further comprises: shearing, drying, and grinding the gelatinous elastic product obtained from the contact reaction in sequence. The drying is preferably carried out at 100-120° C. temperature, and the degree of grinding is determined according to the actual requirement. The shearing, drying, and grinding procedures are known by those skilled in the art, and will not be detailed further here.

According to a preferred embodiment of the present invention, the method for preparation of a hyperbranched copolymer comprises the following steps:

(i) loading water and sodium hydroxide and/or potassium hydroxide in the same moles as a monomer III into a reactor; adding monomer III after they are dissolved, and stirring till the monomer III is dissolved completely; adding the dendritic polymer monomer I, amphoteric ion monomer II, monomer IV, and stirring to a homogeneous state; adjusting the pH value of the system to 7.0-10.0 with 10-20 mass % sodium hydroxide and/or potassium hydroxide solution;

(ii) transferring the reaction mixture prepared in step (i) into a polymer reactor; adding an oxidation-reduction initiating agent while stirring; controlling the initial temperature of polymerization reaction at 20-80° C., preferably 30-60° C., and keeping the polymerization reaction for 20-100 min, preferably 30-90 min, more preferably 45-90 min, to obtain a gelatinous elastic product;

(iii) shearing the gelatinous elastomer obtained in step (ii), drying it at 100-120° C. preferably, and grinding it to obtain a hyperbranched copolymer that can be used as a polymer treating agent for drilling fluids.

wherein the proportions of the raw materials are in the same definitions as those described above, preferably the proportions of the raw materials are:

dendritic polymer monomer I: 0.05~0.25 mole
amphoteric ion monomer II: 0.05~0.30 mole
monomer III: 0.005~0.15 mole
monomer IV: 0.25~0.65 mole
initiating agent (composed of oxidizing agent and reducing agent): 0.10~0.6 g each
water: 95~200 ml Also, the present invention provides a copolymer obtained with the method described above.

Also, the present invention discloses an application of the copolymer in drilling fluids.

Preferably, the copolymer is used as a polymer treating agent for drilling fluids.

When the copolymer provided in the present invention is used as a polymer treating agent for drilling fluids, it exhibits high heat-resistant and salinity-resistant properties, as well as high inhibiting ability, and the product has excellent water-solubility. If the copolymer is prepared with a rapid polymerization method in a water solution, the reaction process can be controlled easily, the operation is easy, the product quality is stable, the energy consumption is very low in the production and drying procedures, and there is no environmental pollution. The copolymer has a favorable filtrate loss reducing property in saturated brine at 180° C. temperature and high-calcium environments, and has no adverse effect to the rheological property and filtrate loss of drilling fluid while ensuring enough inhibiting ability. The main reason for such favorable properties may be that the molecules of the dendritic polymer monomer used in the present invention contain acryloxy that is helpful for polymerization and the molecular chain of the monomer contains amino, carboxy, and sulfonic groups; thus, a hyperbranched polymer can be obtained when the monomer is copolymerized with other monomers. When the hyperbranched polymer is used as a treating agent for drilling fluid, the tackifying effect and stability of the polymer at high temperatures can be improved, owing to the hyperbranched structure of the polymer; since the molecular chain of the large hyperbranched monomer contains amido, carboxy, and sulfonic groups, the hyperbranched polymer has favorable tackifying effect, filtrate loss reducing effect, and inhibiting ability against hydration swelling of shale or clay, when it is used in a drilling fluid.

In the present invention, the apparent viscosity of 1 mass % water solution of the hyperbranched copolymer is measured at 25° C. with a Fann-35 rotary viscosimeter. The contents of the structural units in the hyperbranched copolymer are calculated on the basis of the usages of the monomers.

Hereunder the present invention will be further detailed in some embodiments.

Preparation Example 1

Synthesis of Intermediate

First, an intermediate is synthesized with the conventional method:

(I) methyl acrylate, ethanolamine, and methanol are added at a mole ratio of 1:0.5:15 into a reactor, the mixture is stirred for 30 min at room temperature while $N_2$ is filled, and then is heated up to 35° C. and held for 4 h; then, the mixture is treated by reduced pressure distillation to remove the methanol, so as to obtain a product in the structure denoted by formula (5a);

(II) the product in the structure denoted by formula (5a) and methanol are added at a weight ratio of 1:3 into a reactor, ethylene diamine is added in droplets (the mole ratio of the product in the structure denoted by formula (5a):ethylene diamine is 0.5:1.05) at 25° C. while stirring, the reaction is maintained for 24 h, and then the mixture is treated by reduced pressure distillation to remove the methanol, so as to obtain an intermediate product in the structure denoted by formula (5b);

(III) the intermediate product in the structure denoted by formula (5b) and methanol are added at a weight ratio of 1:3 into a reactor, methyl acrylate is added in droplets (the mole ratio of the product in the structure denoted by formula (5a):methyl acrylate is 0.25:1.05) at 25° C. while stirring, the reaction is maintained for 24 h, and then the mixture is treated by reduced pressure distillation to remove the methanol, so as to obtain an intermediate product in the structure denoted by formula (5c);

(IV) the intermediate product in the structure denoted by formula (5c) and methanol are added at a weight ratio of 1:3 into a reactor, ethylene diamine is added in droplets (the mole ratio of the product in the structure denoted by formula (5a):ethylene diamine is 0.25:1.05) at 25° C. while stirring, the reaction is maintained for 24 h, and then the mixture is treated by reduced pressure distillation to remove the methanol, so as to obtain an intermediate in the structure denoted by formula (5d);

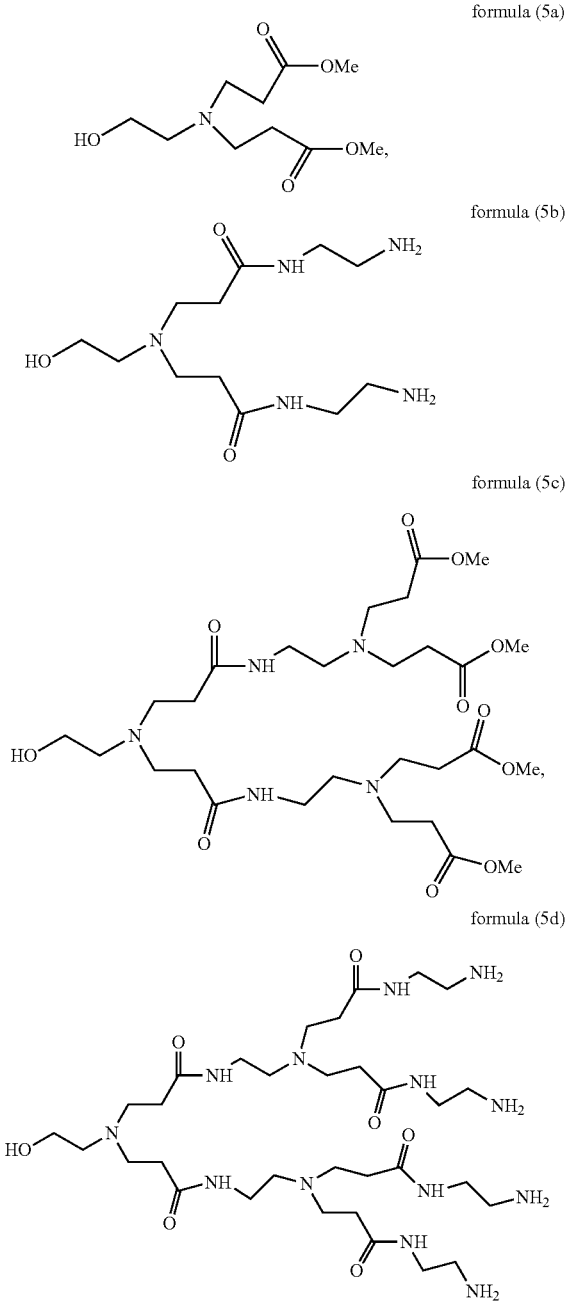

formula (5a)

formula (5b)

formula (5c)

formula (5d)

Preparation Example 2

Synthesis of Intermediate

First, an intermediate is synthesized with the conventional method:

(I) methyl acrylate, ethanolamine, and methanol are added at a mole ratio of 1:0.50:10 into a reactor, the mixture is stirred for 30 min at room temperature while $N_2$ is filled, and then is heated up to 35° C. and held for 4 h; then the mixture is treated by reduced pressure distillation to remove the methanol, so as to obtain a product in the structure denoted by formula (5a);

(II) the product in the structure denoted by formula (5a) and methanol are added at a weight ratio of 1:3.5 into a reactor, ethylene diamine is added in droplets (the mole ratio of the product in the structure denoted by formula (5a):ethylene diamine is 0.5:1.0) at 25° C. while stirring, the reaction is maintained for 24 h, and then the mixture is treated by reduced pressure distillation to remove the methanol, so as to obtain an intermediate product in the structure denoted by formula (5b);

(III) the intermediate product in the structure denoted by formula (5b) and methanol are added at a weight ratio of 1:3.5 into a reactor, methyl acrylate is added in droplets while stirring at 25° C., the reactants are controlled to react for 24 h at that temperature, and then the mixture is treated by reduced pressure distillation to remove the methanol, so as to obtain an intermediate product in the structure denoted by formula (5c);

(IV) the intermediate product in the structure denoted by formula (5c) and methanol are added at a weight ratio of 1:3.5 into a reactor, ethylene diamine is added in droplets while stirring at 25° C., the reactants are controlled to react for 24 h at that temperature, and then the mixture is treated by reduced pressure distillation to remove the methanol, so as to obtain an intermediate product in the structure denoted by formula (5d);

(V) the intermediate product in the structure denoted by formula (5d) and methanol are added at a weight ratio of 1:3.5 into a reactor, methyl acrylate is added in droplets while stirring at 25° C., the reactants are controlled to react for 24 h at that temperature, and then the mixture is treated by reduced pressure distillation to remove the methanol, so as to obtain an intermediate product in the structure denoted by the following formula (6e) (similar to formula (5c), but the generation number is increased by 1);

(VI) the intermediate product obtained in step (V) and methanol are added at a weight ratio of 1:3.5 into a reactor, ethylene diamine is added in droplets while stirring at 25° C., the reactants are controlled to react for 24 h at that temperature, and then the mixture is treated by reduced pressure distillation to remove the methanol, so as to obtain an intermediate in the structure denoted by the following formula (6f).

formula (6e)

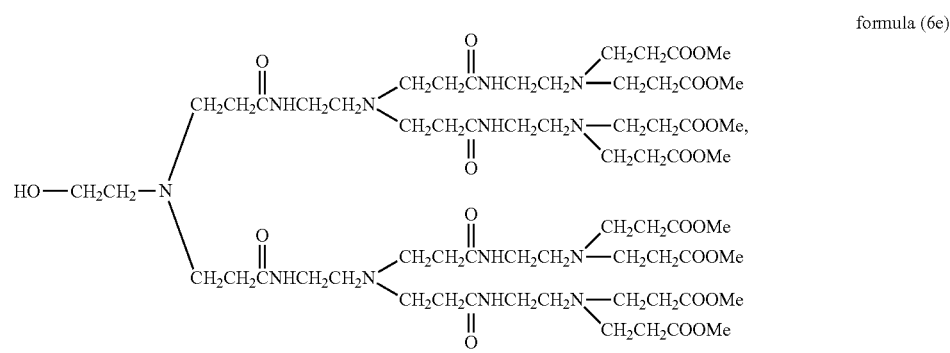

formula (6f)

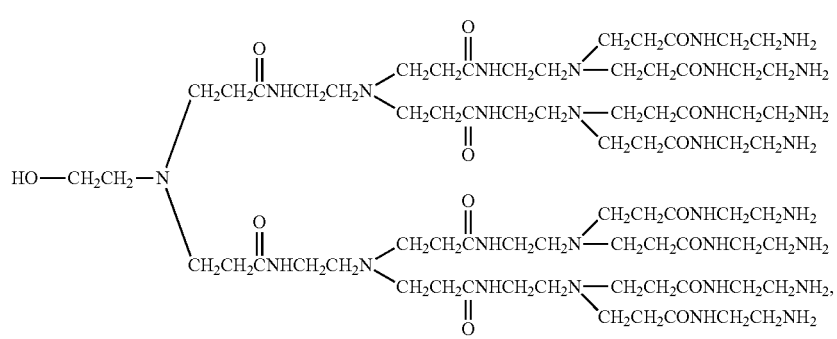

Preparation Example 3

Preparation of Dendritic Polymer Monomer (1) 74.5 g intermediate product in the structure denoted by formula (5d) obtained in the Preparation Example 1 and 180 ml N,N-dimethyl acetamide are added into a reactor, a solution prepared by dissolving 39.2 g maleic anhydride (MA) in 100 ml N,N-dimethyl acetamide is added in droplets at 25° C. while stirring, and then the reactants are heated up to 80° C. and controlled to react for 20 h at that temperature;

(2) 336 g 15 mass % sodium sulfite water solution is added into the reaction product at 30° C., and the reactants are controlled to react for 20 h, till the double bonds disappear (judged by means of bromide addition); then, the reaction product is filtered, and the organic solvent is distilled off; active carbon is added for 24 h absorption treatment; then, the active carbon is filtered off, and the obtained solution is treated by dehydration in vacuum, to obtain a hyperbranched product in the structure denoted by the following formula (I-1):

formula (I-1)

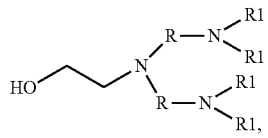

wherein:

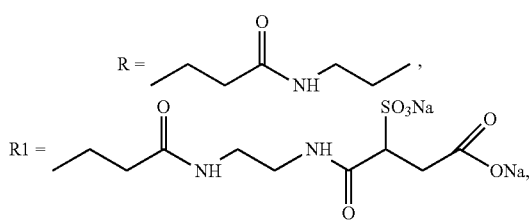

(3) the hyperbranched product obtained in step (2), an organic solvent (dichloromethane), and an acid binding agent (triethylamine) are added into a reaction bulb equipped with a cooling device, the mixture is cooled down to 5° C., and acryloyl chloride is added slowly (the acryloyl chloride is dissolved in a solvent in advance, and the temperature is controlled to be not higher than 15° C. in the adding process), the mole ratio of hyperbranched product: organic solvent:acid binding agent:acryloyl chloride is 1:18:1:1; then, the reactants are controlled to react for 0.5 h at 10° C. after the acryloyl chloride was added; the reactants are kept in still state to separate the organic phase, the organic phase is neutralized and washed with saturated sodium bicarbonate solution for several times, and dried with anhydrous sodium sulfate; then, the organic solvent is distilled off to obtain a crude product; next, the crude product is purified to obtain a polymerized dendritic polymer monomer product in the structure denoted by formula (1-1), wherein $R_1$ is $CH_2CH_2$; $R_2$-$R_4$ and $R_8$-$R_{13}$ are H respectively; M is Na, and both p and q are 0, formula (1-1)

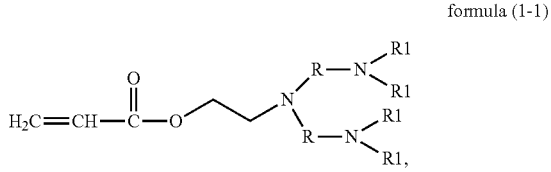

wherein R and R1 are in the same definitions as those described for formula (1-1).

Preparation Example 4

Preparation of Dendritic Polymer Monomer (1) 74.5 g intermediate product in the structure denoted by formula (5d) obtained in the Preparation Example 1 and 150 ml N,N-dimethyl formamide are added into a reactor, a solution prepared by dissolving 39.2 g maleic anhydride (MA) in 110 ml N,N-dimethyl formamide is added in droplets at 30° C. while stirring, the reactants are heated up to 90° C. and controlled to react for 8 h at that temperature;

(2) 421 g 15 mass % potassium sulfite water solution is added into the reaction product at 70° C., and the reactants are controlled to react for 3 h, till the double bonds disappear (judged by means of bromide addition); then, the reaction product is filtered, and the organic solvent is distilled off; active carbon is added for 24 h absorption treatment; then, the active carbon is filtered off, and the obtained solution is treated by dehydration in vacuum, to obtain a hyperbranched product in the structure denoted by the following formula (I-2):

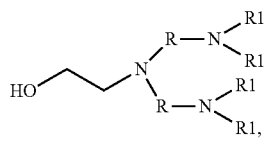

formula (I-2)

wherein:

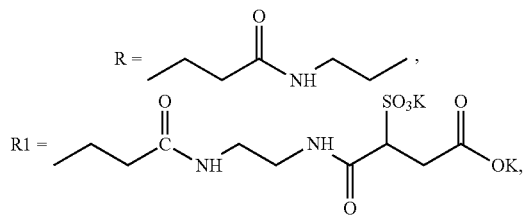

(3) the hyperbranched product obtained in step (2), an organic solvent (N,N-dimethyl acetamide), and an acid binding agent (pyridine) are added into a reaction bulb equipped with a cooling device, the mixture is cooled down to 8° C., and methacrylic chloride is added slowly (the methacrylic chloride is dissolved in a solvent in advance, and the temperature is controlled to be not higher than 15° C. in the adding process), the mole ratio of the hyperbranched product:organic solvent:acid binding agent:acryloyl chloride is 1:20:1.05:1.02; then, the reactants are controlled to react for 0.5 h at 10° C.; the reactants are kept in still state to separate the organic phase, the organic phase is neutralized and washed with saturated sodium bicarbonate solution for several times, and dried with anhydrous sodium sulfate; then, the organic solvent is distilled off to obtain a crude product; next, the crude product is purified to obtain a polymerized dendritic polymer monomer product in the structure denoted by formula (2-2), wherein $R_1$ is $CH_2CH_2$; $R_2$-$R_4$ and $R_8$-$R_{13}$ are H respectively; M is K; and both p and q are 0,

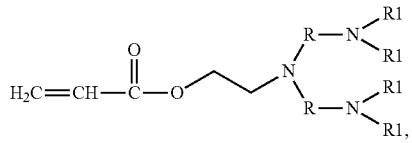

formula (2-2)

wherein R and R1 are in the same definitions as those described for formula (I-2).

Preparation Example 5

Preparation of Dendritic Polymer Monomer (1) 74.5 g intermediate product in the structure denoted by formula (5d) obtained in the Preparation Example 1 and 150 ml N,N-dimethyl acetamide are added into a reactor, a solution prepared by dissolving 56.9 g 3-hexene anhydride in 150 ml N,N-dimethyl acetamide is added in droplets at 25° C. while stirring, the reactants are heated up to 80° C. and controlled to react for 18 h at that temperature;

(2) 336 g 15 mass % sodium sulfite water solution is added into the reaction product, and the reactants are controlled to react, till the double bonds disappear (judged by means of bromide addition); then, the reaction product is filtered, and the organic solvent is distilled off; active carbon is added for 24 h absorption treatment; then, the active carbon is filtered off, and the obtained solution is treated by dehydration in vacuum, to obtain a hyperbranched product in the structure denoted by the following formula (I-3):

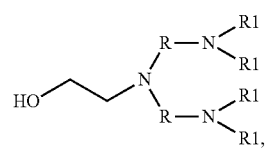

formula (I-3)

wherein:

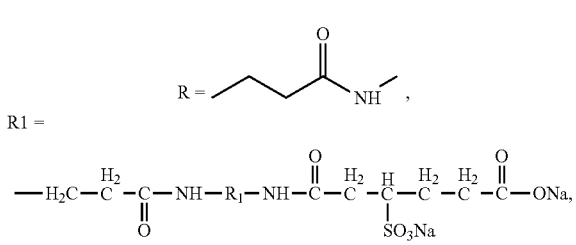

(3) the hyperbranched product obtained in step (2), an organic solvent (methyl benzene), and an acid binding agent (triethylamine) are added into a reaction bulb equipped with a cooling device, the mixture is cooled down to 0° C., and acroloyl bromide is added slowly (the acroloyl bromide is dissolved in a solvent in advance, and the temperature is controlled to be not higher than 15° C. in the adding process), the mole ratio of the hyperbranched product: organic solvent:acid binding agent:acryloyl bromide is 1:22: 1.1:1.05; then the reactants are controlled to react for 0.5 h at 10° C.; the reactants are kept in still state to separate the organic phase, the organic phase is neutralized and washed with saturated sodium bicarbonate solution for several times, and dried with anhydrous sodium sulfate; then the organic solvent is distilled off to obtain a crude product; next the crude product is purified to obtain a polymerized dendritic polymer monomer product in the structure denoted by formula (2-3), wherein $R_1$ is $CH_2CH_2$; $R_2$-$R_4$ and $R_8$-$R_{13}$ are H respectively; M is Na; and both p and q are 1,

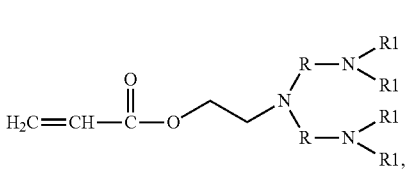

formula (2-3)

wherein R and R1 are in the same definitions as those described for formula (I-3).

Preparation Example 6

Preparation of Dendritic Polymer Monomer (1) 82.85 g intermediate in the structure denoted by formula (61) obtained in the Preparation Example 2 and 200 ml N,N-dimethyl acetamide are added into a reactor, a solution prepared by dissolving 39.2 g maleic anhydride (MA) in 120 ml N,N-dimethyl acetamide is added in droplets at 25° C. while stirring, the reactants are heated up to 80° C. and controlled to react for 15 h at that temperature;

(2) 336 g 15 mass % sodium sulfite water solution is added into the reaction product at 60° C., and the reactants are controlled to react for 18 h, till the double bonds disappear (judged by means of bromide addition); then, the reaction product is filtered, and the organic solvent is distilled off; active carbon is added for 24 h absorption treatment; then, the active carbon is filtered off, and the obtained solution is treated by dehydration in vacuum, to obtain a hyperbranched product in the structure denoted by the following formula (I-4):

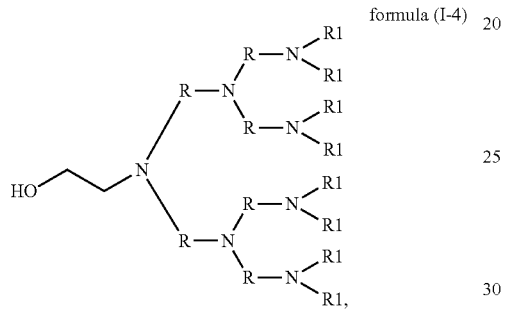

formula (I-4)

wherein:

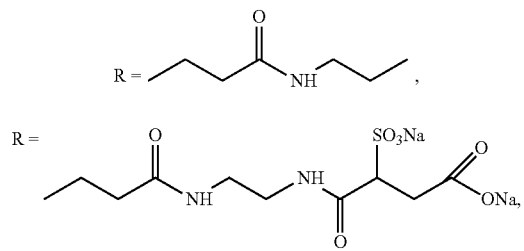

(3) the hyperbranched product obtained in step (2), an organic solvent (dichloromethane), and an acid binding agent (triethylamine) are added into a reaction bulb equipped with a cooling device, the mixture is cooled down to 5° C., and acryloyl chloride is added slowly (the acryloyl chloride is dissolved in a solvent in advance, and the temperature is controlled to be not higher than 15° C. in the adding process), the mole ratio of the hyperbranched product:organic solvent:acid binding agent:acryloyl chloride=1:18:1:1; then the reactants are controlled to react for 0.5 h at 10° C.; the reactants are kept in still state to separate the organic phase, the organic phase is neutralized and washed with saturated sodium bicarbonate solution for several times, and dried with anhydrous sodium sulfate; then, the organic solvent is distilled off to obtain a crude product; next the crude product is purified to obtain a polymerized dendritic polymer monomer product in the structure denoted by formula (2-4), wherein $R_1$ is $CH_2CH_2$; $R_2$-$R_4$ and $R_8$-$R_{13}$ are H respectively; M is Na; and both p and q are 0,

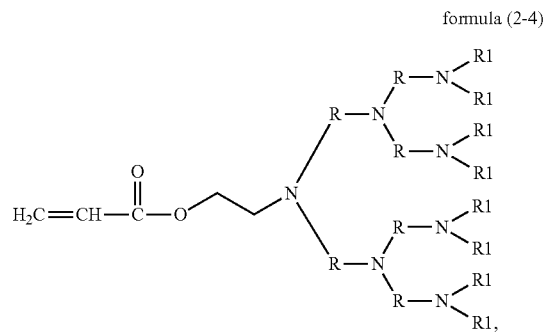

formula (2-4)

wherein R and R1 are in the same definitions as those described for formula (I-4).

Example 1

Preparation of Hyperbranched Copolymer 200 ml water and 0.05 mole sodium hydroxide are loaded into a reactor; after they are dissolved, 0.05 mole 2-acrylamide-2-methyl propanesulfonic acid is added and the mixture is stirred to homogeneous state; the pH value of the system is adjusted to 10.0 with 20 mass % sodium hydroxide solution; then, 0.25 mole dendritic polymer monomer prepared in the Preparation Example 3, 0.05 mole 3-acrylamide propyl dimethyl ammonium propylsulfonate, and 0.65 mole acrylamide are added, and the mixture is stirred to facilitate dissolving, so as to obtain a reaction mixture solution; the reaction mixture solution is transferred into a polymerization reactor, and 0.10 g ammonium persulfate and 0.10 g sodium bisulfite are added while stirring; the initial temperature of polymerization reaction is controlled at 60° C., and the reaction is maintained for 45 min to obtain a gelatinous elastic product; the obtained gelatinous elastomer is sheared, dried at 120° C., and ground, to obtain a polymer treating agent for drilling fluids. The apparent viscosity of 1 mass % water solution of the polymer treating agent for drilling fluids is 58.5 mPa·s.

The heat-resistance and salinity-resistance of the polymer treating agent is evaluated by testing the filtrate loss reduction property in compounding brine. The base mud of compounding brine is prepared as follows: 15.75 g sodium chloride, 1.75 g anhydrous calcium chloride, 4.6 g magnesium chloride, 52.5 g calcium bentonite (an industrial product from Weifang Haoda Bentonite Co. Ltd.), and 3.15 g anhydrous sodium carbonate are added into 350 ml distilled water, the mixture is stirred for 20 min at a high speed, and held for 24 h at room temperature, to obtain a base mud of compounding brine. In the evaluation process, 1.5 wt % specimen is added, the mixture is stirred for 5 min at a high speed, and then treated by rolled aging for 16 h at 180° C. and cooled to room temperature; then the filtrate loss of the drilling fluid is measured with a ZNS drilling fluid filtration press. The API filtrate loss is 228 ml after the base mud is treated by rolled aging for 16 h at 180° C.

The inhibiting ability and adsorptive capacity of the polymer treating agent are tested with a rolling recovery method for shale. The method is as follows:

Primary recovery rate $R_1$: 50 g shale debris sample (m) is weighed accurately, and added into 350 ml 0.3 mass % polymer solution to be measured; then, the solution is loaded into an aging can, sealed, and rolled for 16 h at 120° C.; next, the solution is cooled down, and the debris is recovered through a 40-mesh sieve; the recovered debris is baked at 100±5° C. to constant mass, and is weighed ($m_1$); then the primary recovery rate $R_1$ is calculated. The primary recovery rate reflects the hydration dispersion of the shale in the water solution of treating agent; the higher the primary recovery rate $R_1$ is, the higher the inhibiting ability will be.

Secondary recovery rate $R_2$: the debris ($m_1$) obtained in the primary recovery process is added into 350 ml clean water, the mixture is rolled for 2 h at 120° C. and then is cooled down, the debris is recovered through a 40-mesh sieve, the recovered debris is baked at 100±5° C. to constant mass, and then is weighed ($m_2$); next the secondary recovery rate $R_2$ is calculated. The secondary recovery rate reflects the stability of the debris obtained in the primary recovery process in clean water; the higher the secondary recovery rate is, the higher the adsorptive capacity of the treating agent will be.

The debris is obtained at 2,695 m in open well 9-5 (at 6~10-mesh size). The recovery rate of the clean water (without specimen) for debris is 49.5%.

The calculation formulae are as follows:

$$R_1 = \frac{m_1}{m} \times 100\%, \quad R_2 = \frac{m_2}{m_1} \times 100\%, \quad R = \frac{R_2}{R_1} \times 100\%,$$

wherein R is a relative recovery rate, which reflects the adsorptive capacity of the polymer on the shale; the higher the value is, the higher the adsorptive capacity will be.

The solubility is judged on the basis of the time of high speed stirring required for forming homogeneous water solution (i.e., without swelling particles of polymer) when 0.5 mass % water solution of the polymer is prepared at room temperature. The process is as follows: 2 g specimen is added into 398 ml water while stirring at a high speed, and then the stirring is continued; after the mixing time reaches 3 min, the dissolution state is observed once every 30 s, till the specimen is dissolved completely; finally, the mixing time required for complete dissolution is recorded.

The tackifying ability of $CaCl_2$ solution is evaluated on the basis of the viscosity ratio of 0.3 mass % $CaCl_2$ water solution of the polymer (with 20% mass $CaCl_2$) vs. water solution of the polymer, i.e. the viscosity retentivity:

Viscosity retentivity =

$$\frac{\text{Viscosity of } CaCl_2 \text{ water solution of the polymer}}{\text{Viscosity of water solution of the polymer}} \times 100\%$$

The test result is shown in Table 1 below.

Example 2

Preparation of Hyperbranched Copolymer 95 ml water and 0.15 mole sodium hydroxide are loaded into a reactor; after they are dissolved, 0.15 mole 2-acrylamide-2-methyl propanesulfonic acid is added and the mixture is stirred to homogeneous state; the pH value of the system is adjusted to 7.0 with 10 mass % potassium hydroxide solution; then, 0.05 mole dendritic polymer monomer prepared in the Preparation Example 4, 0.30 mole 3-acrylamide propyl dimethyl ammonium propylsulfonate, and 0.25 mole acrylamide are added, and the mixture is stirred to facilitate dissolving, so as to obtain a reaction mixture solution; the reaction mixture solution is transferred into a polymerization reactor, and 0.30 g ammonium persulfate and 0.30 g sodium bisulfite are added while stirring; the initial temperature of polymerization reaction is controlled at 40° C., and the reaction is maintained for 90 min, to obtain a gelatinous elastic product; the obtained gelatinous elastomer is sheared, dried at 100° C., and ground, to obtain a polymer treating agent for drilling fluids. The apparent viscosity of 1 mass % water solution of the polymer treating agent for drilling fluids is 42.5 mPa·s.

Performance test is carried out with the method described in Example 1, and the result is shown in Table 1 below.

Example 3

Preparation of Hyperbranched Copolymer 185 ml water and 0.1 mole sodium hydroxide are loaded into a reactor; after they are dissolved, 0.10 mole 2-acrylamide-2-methyl propanesulfonic acid is added into the reactor and the mixture is stirred to homogeneous state; the pH value of the system is adjusted to 8.0 with 15 mass % sodium hydroxide solution; then, 0.20 mole dendritic polymer monomer prepared in the Preparation Example 5, 0.30 mole 3-acrylamide propyl (2-hydroxy)-propyl dimethyl ammonium chloride, and 0.30 mole acrylamide are added, and the mixture is stirred to facilitate dissolving, so as to obtain a reaction mixture solution; the reaction mixture solution is transferred into a polymerization reactor, and 0.35 g potassium persulfate and 0.35 g sodium bisulfite are added while stirring; the initial temperature of polymerization reaction is controlled at 45° C., and the reaction is maintained for 60 min, to obtain a gelatinous elastic product; the obtained gelatinous elastomer is sheared, dried at 110° C., and ground, to obtain a polymer treating agent for drilling fluids.

Performance test is carried out with the method described in Example 1, and the result is shown in Table 1 below. The apparent viscosity of 1 mass % water solution of the polymer treating agent for drilling fluids is 51 mPa·s.

Example 4

Preparation of Hyperbranched Copolymer 180 ml water and 0.1 mole sodium hydroxide are loaded into a reactor; after they are dissolved, 0.10 mole 2-acrylamide-2-methyl propanesulfonic acid is added into the reactor and the mixture is stirred to homogeneous state; the pH value of the system is adjusted to 8.0 with 12 mass % potassium hydroxide solution; then, 0.20 mole dendritic polymer monomer prepared in the Preparation Example 6, 0.35 mole 3-acrylamide propyl dimethyl ammonium allylsulfonate, and 0.30 mole acrylamide are added, and the mixture is stirred to facilitate dissolving, so as to obtain a reaction mixture solution; the reaction mixture solution is transferred into a polymerization reactor, and 0.35 g ammonium persulfate and 0.35 g sodium bisulfite are added while stirring; the initial temperature of polymerization reaction is controlled at 45° C., and the reaction is maintained for 60 min, to obtain a gelatinous elastic product; the obtained gelatinous elastomer is sheared, dried at 120° C., and ground, to obtain a polymer treating agent for drilling fluids. The apparent viscosity of 1 mass % water solution of the polymer treating agent for drilling fluids is 53.5 mPa·s.

Performance test is carried out with the method described in Example 1, and the result is shown in Table 1 below.

Comparative Example 1

A polymer treating agent for drilling fluids is prepared with the method described in Example 1, but the dendritic polymer monomer prepared in the Preparation Example 3 is not added for polymerization reaction; in that way, a reference polymer treating agent for drilling fluids is obtained. Performance test is carried out with the method described in example 1, and the result is shown in Table 1 below.

TABLE 1

| Polymer Treating Agent | | Example 1 | Example 2 | Example 3 | Example 4 | Comparative Example 1 |
|---|---|---|---|---|---|---|
| Dendritic polymer monomer | | Preparation Example 3 | Preparation Example 4 | Preparation Example 5 | Preparation Example 6 | — |
| Heat-resistance and salinity-resistance | | 14.5 ml | 13.7 ml | 13.8 ml | 18 ml | 89 ml |
| Inhibiting ability | $R_1$, % | 96.1 | 95.9 | 96.0 | 95.7 | 91.5 |
| | $R_2$, % | 95.4 | 95.1 | 95.1 | 94.5 | 80.2 |
| | $R_2/R_1$, % | 99.27 | 99.17 | 99.06 | 98.75 | 87.65 |
| Viscocity retentivity, % | | 34.5 | 33.6 | 35.0 | 31.7 | 15.2 |

Note:
The API filtrate loss is 228 ml after the base mud is treated by rolled aging for 16 h at 180° C. The recovery rate of the clean water (without specimen) for debris is 49.5%.

Examples 5-9

In Examples 5-9, a hyperbranched copolymer is prepared with the method described in Example 1 respectively, but the amphoteric ion monomer II and oxidation-reduction initiating agent used in the preparation process are changed to those shown in Table 2 below. The apparent viscosity values of 1 mass % water solutions of the obtained polymer treating agents for drilling fluids are 54.5 mPa·s, 53.0 mPa·s, 55.5 mPa·s, 54.0 mPa·s, and 55 mPa·s respectively. Performance test is carried out with the method described in example 1, and the result is shown in Table 3 below.

TABLE 2

| | | Example | | | |
|---|---|---|---|---|---|
| | Example 5 | Example 6 | Example 7 | Example 8 | Example 9 |
| Amphoteric ion monomer | ① | ② | ③ | ④ | ⑤ |
| Initiator Oxidizing agent | | | | | potassium persulfate |

TABLE 2-continued

| | | Example | | | |
|---|---|---|---|---|---|
| | Example 5 | Example 6 | Example 7 | Example 8 | Example 9 |
| Reducer | sodium pyrosulfite | sodium thiosulfate | sodium sulfite | | |

Note:
①: 3-acryloxy ethyl dimethyl ammonium propylsulfonate,
②: 3-acryloxy ethyl diethyl ammonium propylsulfonate,
③: 3-acryloxy ethyl diisopropyl ammonium propylsulfonate,
④: 3-acrylamide propyl trimethyl ammonium chloride,
⑤: 3-acryloxy propyl trimethyl ammonium chloride

TABLE 3

| Polymer Treating Agent | | Example 5 | Example 6 | Example 7 | Example 8 | Example 9 |
|---|---|---|---|---|---|---|
| Dendritic polymer monomer | | Preparation Example 3 | Preparation Example 3 | Preparation Example 3 | Preparation Example 3 | Preparation Example 3 |
| Heat-resistance and salinity-resistance | | 14.1 | 13.8 | 13.6 | 12.9 | 13.4 |
| Inhibiting ability | $R_1$, % | 96.2 | 96.1 | 95.8 | 95.7 | 95.9 |
| | $R_2$, % | 95.5 | 95.2 | 95.1 | 94.9 | 95.1 |
| | $R_2/R_1$, % | 99.27 | 99.06 | 99.27 | 99.16 | 99.17 |
| Viscocity retentivity, % | | 34.4 | 34.6 | 34.5 | 34.2 | 34.3 |

Note:
The API filtrate loss is 228 ml after the base mud is treated by rolled aging for 16 h at 180° C. The recovery rate of the clean water (without specimen) for debris is 49.5%.

The results in Table 1 and Table 3 demonstrate that the polymer treating agent in the present invention prepared from dendritic polymer monomer and other monomers has high heat-resistance and salinity-resistance properties, and favorable inhibiting ability, and the product has high water-solubility.

While some preferred embodiments of the present invention are described above, the present invention is not limited to the details in those embodiments. Those skilled in the art can make modifications and variations to the technical scheme of the present invention, without departing from the spirit of the present invention. However, all these modifications and variations shall be deemed as falling into the protected domain of the present invention.

In addition, it should be appreciated that the technical features described in the above embodiments can be combined in any appropriate manner, provided that there is no conflict among the technical features in the combination. To avoid unnecessary iteration, such possible combinations are not described here in the present invention.

Moreover, different embodiments of the present invention can be combined freely as required, as long as the combinations don't deviate from the ideal and spirit of the present invention. However, such combinations shall also be deemed as falling into the scope disclosed in the present invention.

The invention claimed is:

1. A dendritic polymer, having a structure denoted by Z-(Q)n-Y, wherein Z represents a group that can have condensation reaction with an acyl halide, Q represents a dendritic constitutional repeating unit of the dendritic polymer, n represents a generation number of the dendritic polymer, and is an integer within a range of 2-6, and Y represents a group containing $SO_3^-$ and $COO^-$.

2. The dendritic polymer according to claim 1, wherein Z is OH or $NH_2$, Q is a structure denoted by the following formula (I), and Y is a structure denoted by the following formula (II),

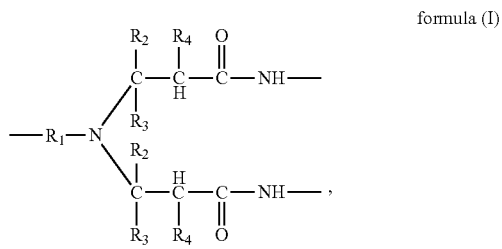

formula (I)

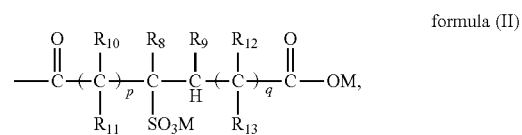

formula (II)

in formula (I), $R_1$ represents $C_2$-$C_5$ alkylene, $R_2$-$R_4$ can be identical to or different from each other, and are H or $C_1$-$C_5$ alkyl respectively; in addition, for n structures denoted by formula (I), $R_1$-$R_4$ can be identical to or different from each other;

in formula (II), $R_8$-$R_{13}$ can be identical to or different from each other, and are H or $C_1$-$C_5$ alkyl respectively, p and q can be identical to or different from each other, and are an integer within a range of 0-5 respectively, and M is H, Na, or K.

3. The dendritic polymer according to claim 2, having a structure denoted by the following formula (III) or formula (IV),

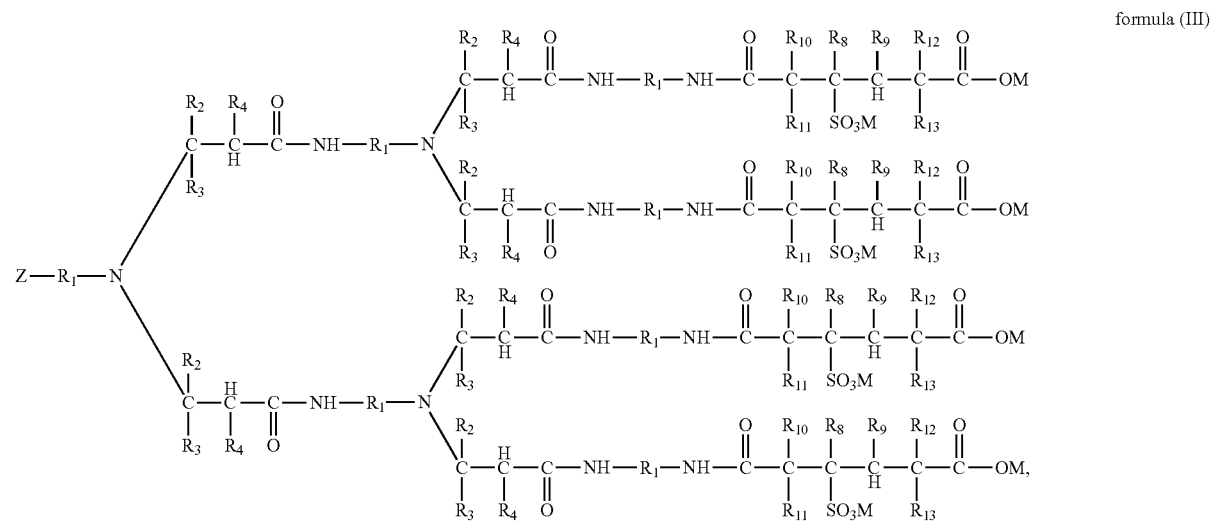

formula (III)

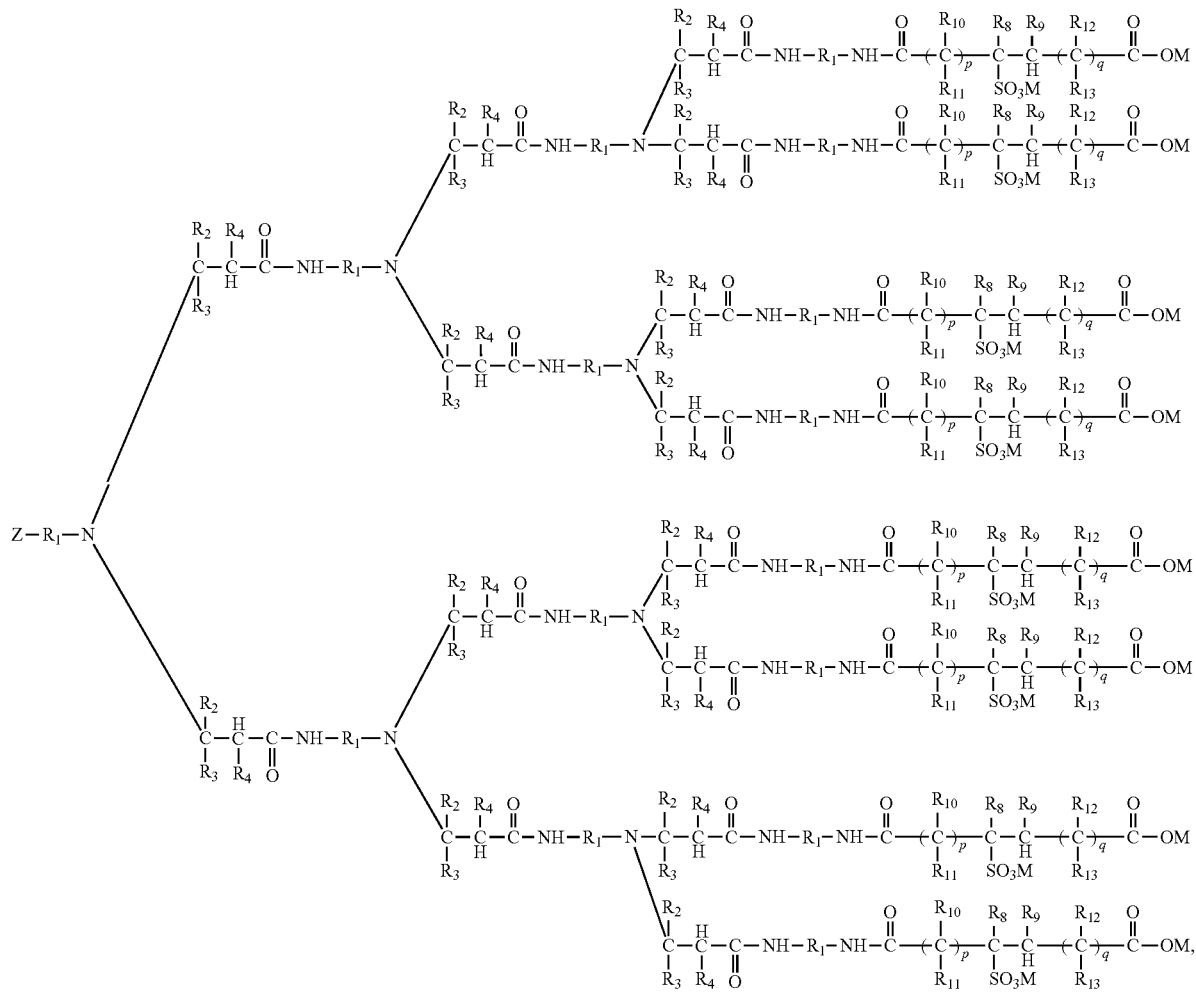

formula (IV)

wherein Z, $R_1$-$R_4$, $R_8$-$R_{13}$, M, p, and q are in the same definitions as those described in claim 2.

4. The dendritic polymer according to claim 2, wherein Z is OH; $R_1$ is $CH_2CH_2$; all of $R_2$-$R_4$ and $R_8$-$R_{13}$ are H; M is Na or K; and both p and q are 0 or 1.

5. The dendritic polymer according to claim 3, wherein Z is OH; $R_1$ is $CH_2CH_2$; all of $R_2$-$R_4$ and $R_8$-$R_{13}$ are H; M is Na or K; and both p and q are 0 or 1.

6. The dendritic polymer according to claim 1, wherein Y is free of a C=C bond.

* * * * *